US008818497B2

(12) United States Patent
Yamazaki

(10) Patent No.: US 8,818,497 B2
(45) Date of Patent: Aug. 26, 2014

(54) BIOLOGICAL SIGNAL PROCESSING UNIT, WIRELESS MEMORY, BIOLOGICAL SIGNAL PROCESSING SYSTEM, AND CONTROL SYSTEM OF DEVICE TO BE CONTROLLED

(75) Inventor: Shunpei Yamazaki, Setagaya (JP)

(73) Assignee: Semiconductor Energy Laboratory Co., Ltd., Atsugi-shi, Kanagawa-ken (JP)

(*) Notice: Subject to any disclaimer, the term of this patent is extended or adjusted under 35 U.S.C. 154(b) by 525 days.

(21) Appl. No.: 11/631,159

(22) PCT Filed: Jul. 12, 2005

(86) PCT No.: PCT/JP2005/013211
§ 371 (c)(1),
(2), (4) Date: Dec. 29, 2006

(87) PCT Pub. No.: WO2006/009129
PCT Pub. Date: Jan. 26, 2006

(65) Prior Publication Data
US 2008/0294033 A1 Nov. 27, 2008

(30) Foreign Application Priority Data

Jul. 16, 2004 (JP) .................. 2004-210405

(51) Int. Cl.
*A61B 5/04* (2006.01)
*A61F 4/00* (2006.01)
*A61B 5/0478* (2006.01)
*G06F 3/01* (2006.01)
*A61B 5/00* (2006.01)

(52) U.S. Cl.
CPC . *G06F 3/015* (2013.01); *A61F 4/00* (2013.01); *A61B 5/0478* (2013.01); *A61B 5/6814* (2013.01)
USPC .......................................... 600/544; 600/545

(58) Field of Classification Search
USPC .................................................. 600/544–545
See application file for complete search history.

(56) References Cited

U.S. PATENT DOCUMENTS 3,753,433 A * 8/1973 Bakerich et al. ............... 600/545
3,951,134 A * 4/1976 Malech .......................... 600/544
(Continued)

FOREIGN PATENT DOCUMENTS

EP          0 925 756        6/1999
EP          0993032 A        4/2000
(Continued)

OTHER PUBLICATIONS

International Search Report (Application No. PCT/JP2005/013211) dated Nov. 1, 2005.

(Continued)

*Primary Examiner* — Michael D'Angelo
(74) *Attorney, Agent, or Firm* — Eric J. Robinson; Robinson Intellectual Property Law Office, P.C.

(57) ABSTRACT

It is an object to provide a means for easily operating various devices to be controlled (i.e. a word processor or a car) using a brain wave signal of a patient with Alzheimer's disease or a psychological disorder, and for supporting the active performance of a user by employing wireless communication with a memory (wireless memory) capable of communicating without wires in which a command on the human movement is memorized. A present biological signal processing unit has an electrode for detecting a biological signal (an electric signal) from a living body, or for transmitting an electric signal into a living body, an interface, and an antenna which can communicate with an external device (i.e. wireless memory, reader/writer); therefore, convenience of the user is improved in the case where a user utilizes an electronic device or the like. In addition, the active performance of a user can be supported.

34 Claims, 13 Drawing Sheets

(56) References Cited

U.S. PATENT DOCUMENTS

| | | | |
|---|---|---|---|
| 5,038,782 A * | 8/1991 | Gevins et al. | 600/383 |
| 5,321,286 A * | 6/1994 | Koyama et al. | 257/315 |
| 5,559,042 A * | 9/1996 | Yamazaki et al. | 438/164 |
| 5,862,803 A * | 1/1999 | Besson et al. | 600/508 |
| 5,917,772 A * | 6/1999 | Pawlowski | 365/230.03 |
| 6,161,036 A | 12/2000 | Matsumura et al. | |
| 6,389,309 B1 | 5/2002 | Matsumura et al. | |
| 6,656,779 B1 | 12/2003 | Kasahara | |
| 6,856,832 B1 | 2/2005 | Matsumura et al. | |
| 7,089,048 B2 | 8/2006 | Matsumura et al. | |
| 7,138,657 B2 | 11/2006 | Kasahara | |
| 7,367,992 B2 | 5/2008 | Dadd | |
| 2002/0103441 A1 | 8/2002 | Matsumura et al. | |
| 2003/0004428 A1* | 1/2003 | Pless et al. | 600/544 |
| 2003/0208113 A1* | 11/2003 | Mault et al. | 600/316 |
| 2004/0030258 A1* | 2/2004 | Williams et al. | 600/544 |
| 2004/0097824 A1* | 5/2004 | Kageyama | 600/544 |
| 2004/0116995 A1 | 6/2004 | Dadd | |
| 2004/0249302 A1 | 12/2004 | Donoghue et al. | |
| 2005/0107714 A1 | 5/2005 | Matsumura et al. | |
| 2005/0113744 A1 | 5/2005 | Donoghue et al. | |
| 2005/0119581 A1 | 6/2005 | Matsumura et al. | |
| 2005/0119582 A1 | 6/2005 | Matsumura et al. | |
| 2005/0143669 A1 | 6/2005 | Matsumura et al. | |
| 2007/0063199 A1 | 3/2007 | Kasahara | |
| 2007/0265543 A1* | 11/2007 | VanSickle et al. | 600/544 |

FOREIGN PATENT DOCUMENTS

| | | |
|---|---|---|
| EP | 2264745 A | 12/2010 |
| JP | 05-115451 A | 5/1993 |
| JP | 08-196516 | 8/1996 |
| JP | 2000-183360 A | 6/2000 |
| JP | 2001-078974 | 3/2001 |
| JP | 2003-111739 | 4/2003 |
| JP | 2003-111739 A | 4/2003 |
| JP | 2004-152002 | 5/2004 |
| WO | WO-02/071984 | 9/2002 |

OTHER PUBLICATIONS

Written Opinion (Application No. PCT/JP2005/013211) dated Nov. 1, 2005.

L. Sandhana, *Directly Coupled Brain and Computer, New Interface Capable of Handling Wheelchair by Just Thinking*, Wired News, Jul. 30, 2003, Internet <URL: http://hotwired.goo.ne.jp/news/technology/story/20030801301.html >.

L. Sandhana, *I Think, Therefore I Communicate*, Wired News, Jul. 30, 2003, Internet <URL: http://www.wired.com/news/print/0,1294,59737,00.html >.

European Search Report (Application No. 05762040.3) Dated Nov. 5, 2010.

* cited by examiner

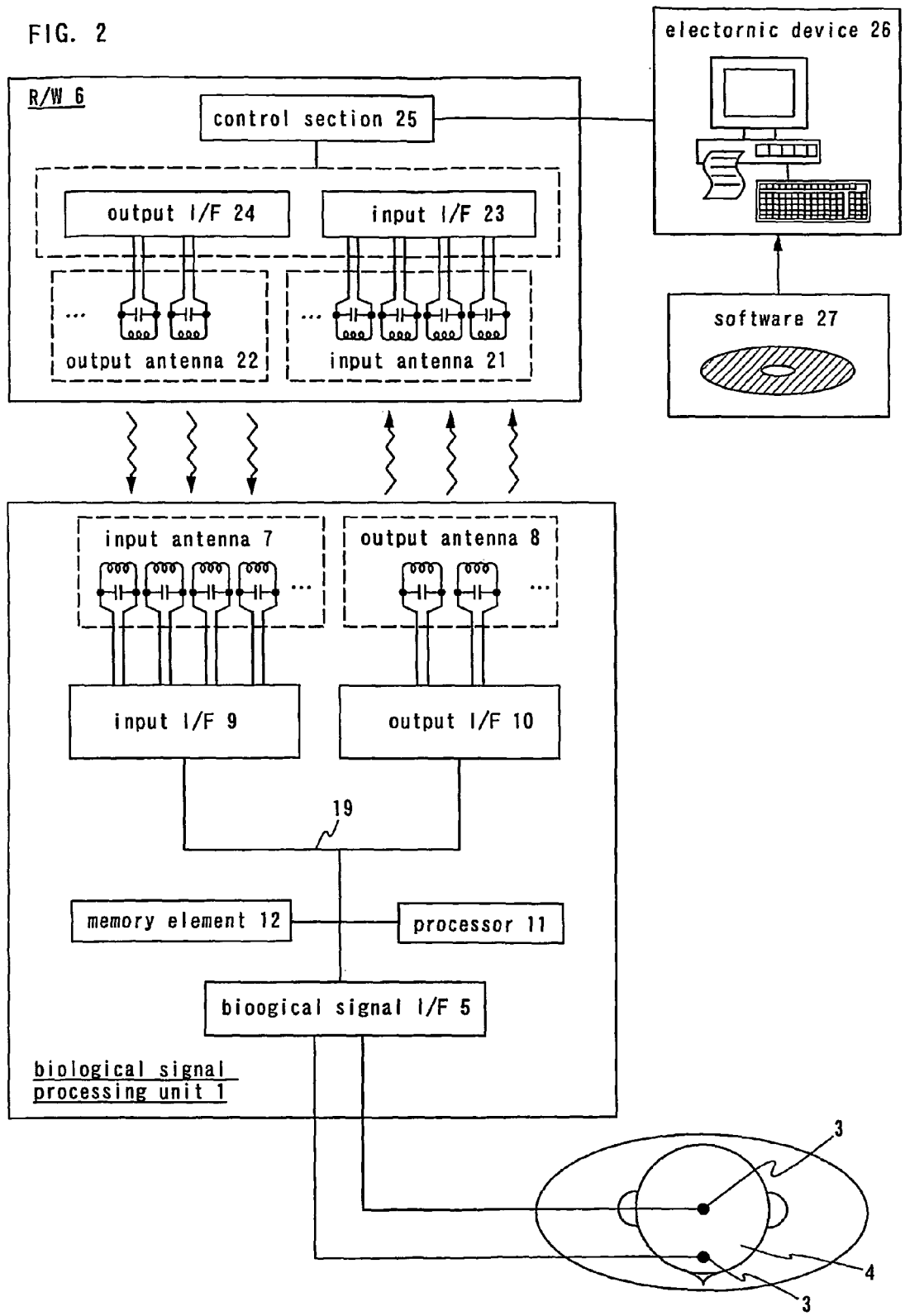

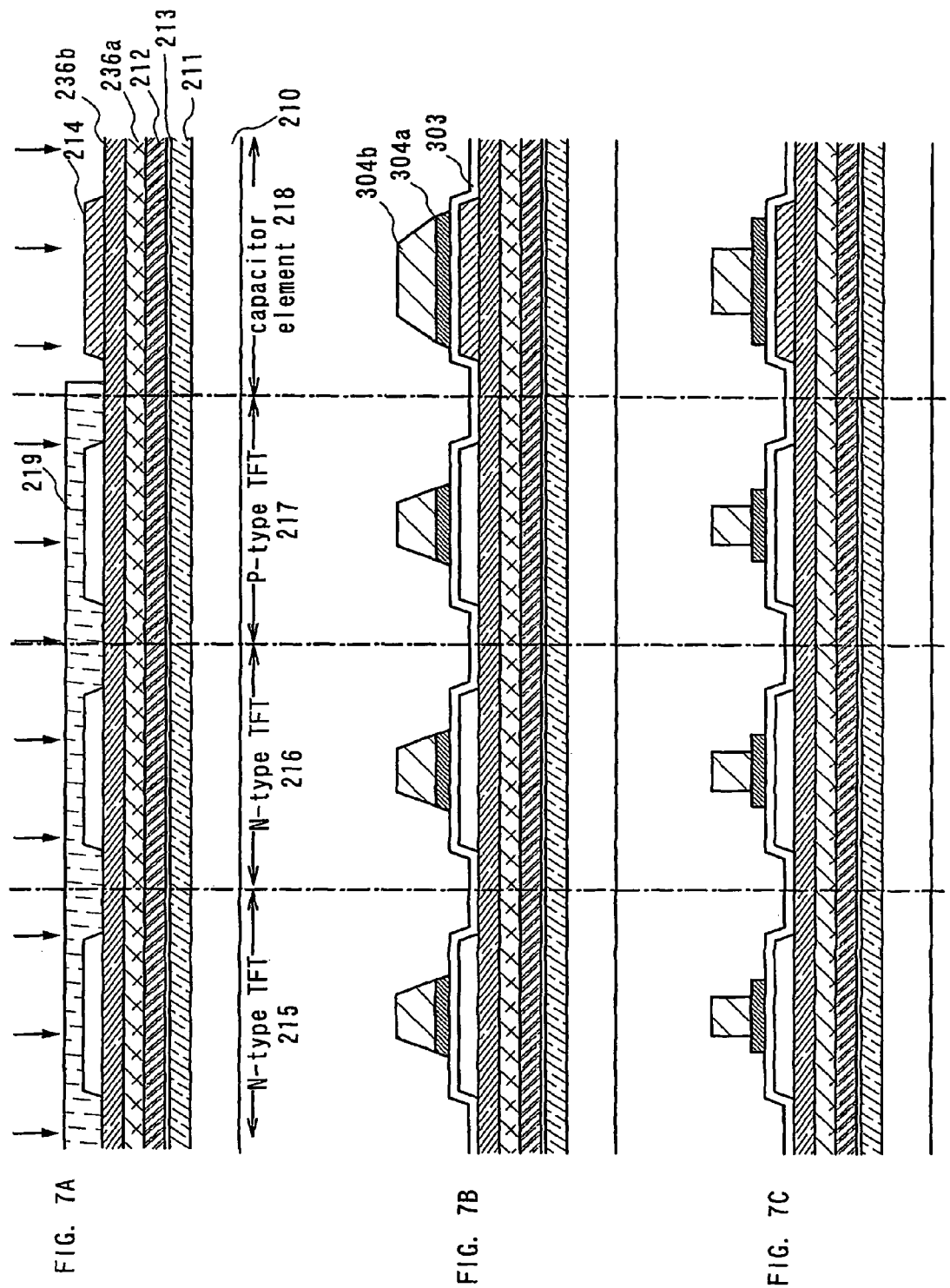

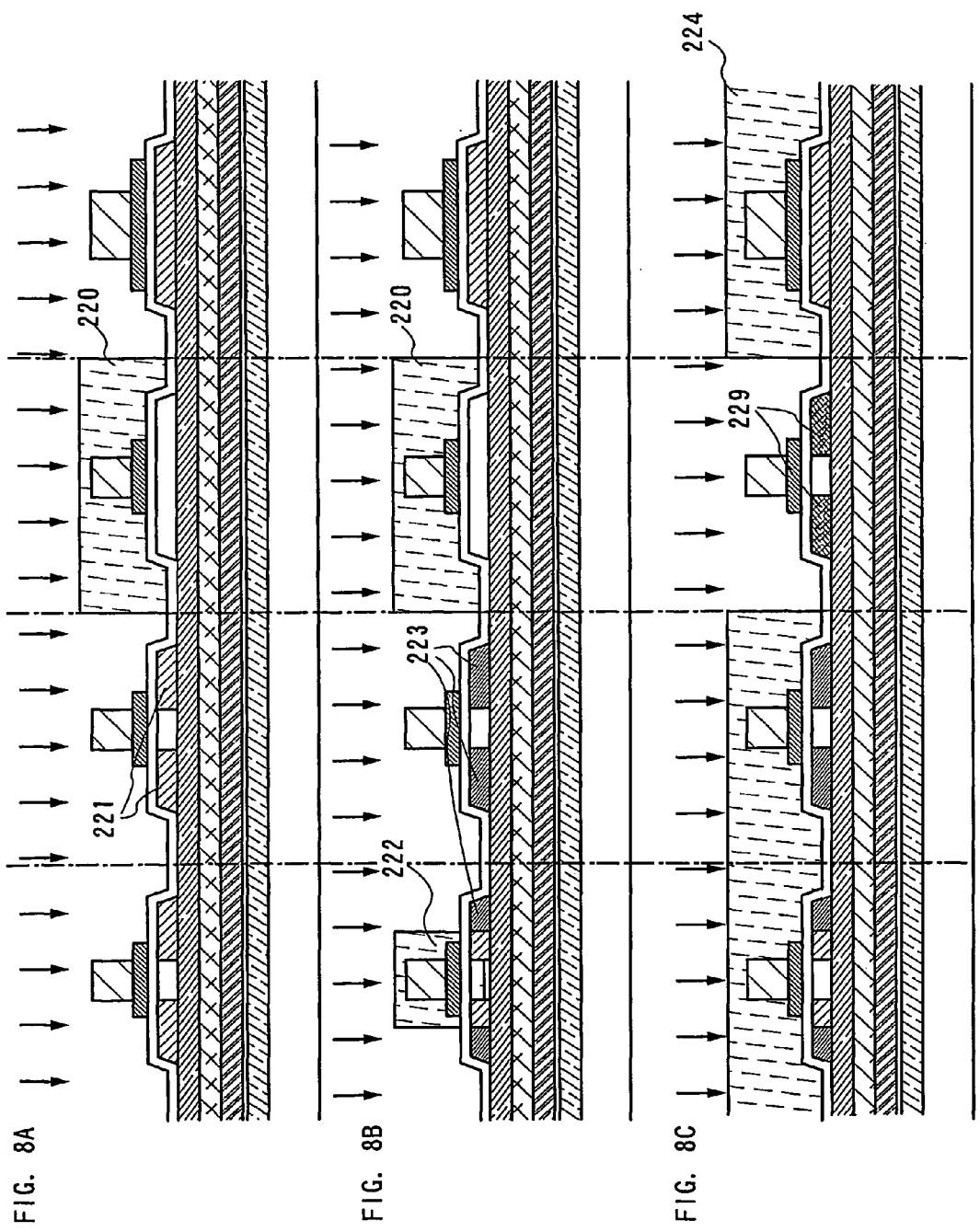

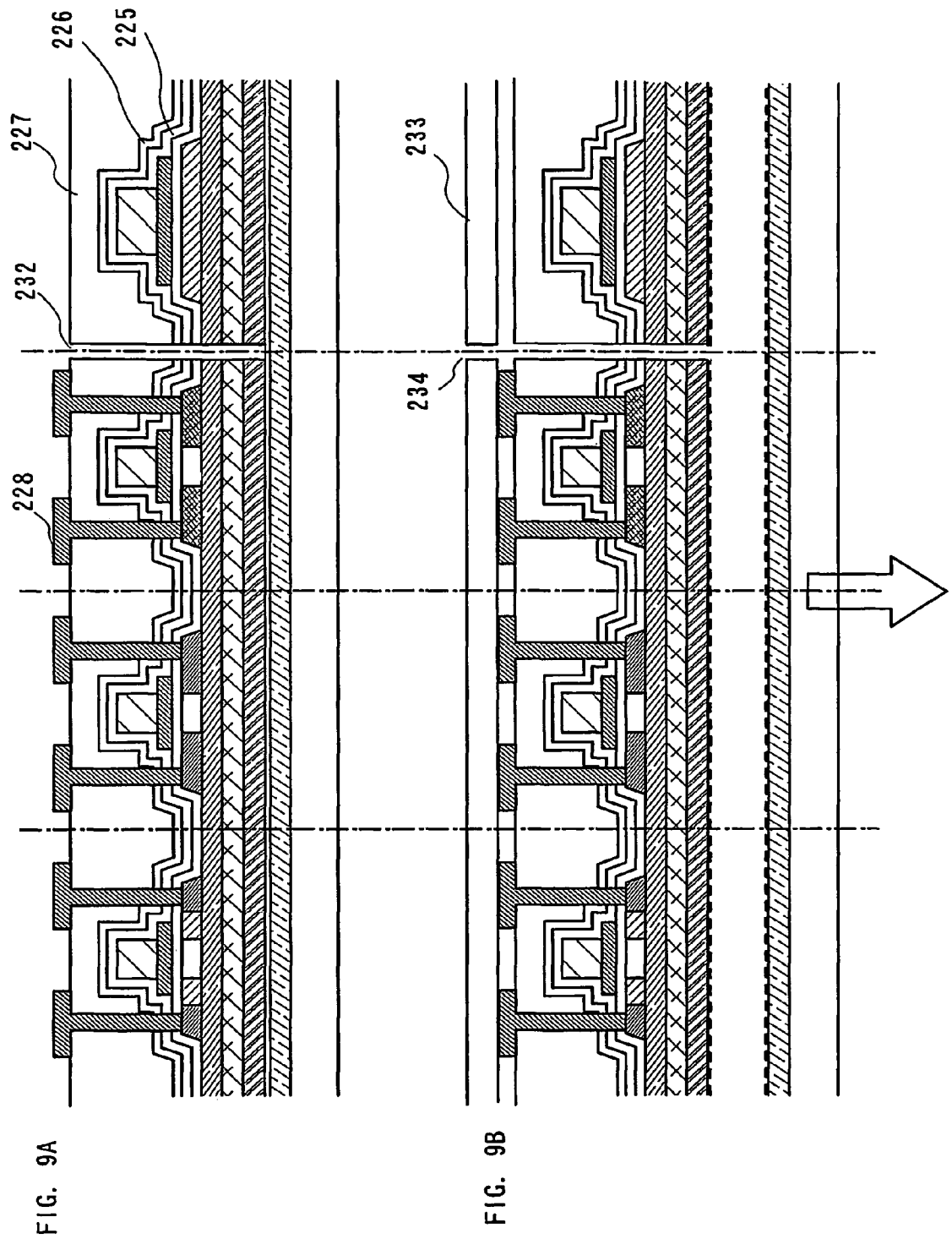

BIOLOGICAL SIGNAL PROCESSING UNIT, WIRELESS MEMORY, BIOLOGICAL SIGNAL PROCESSING SYSTEM, AND CONTROL SYSTEM OF DEVICE TO BE CONTROLLED

TECHNICAL FIELD

The present invention relates to a biological signal processing unit which can detect a biological signal (electric signal) from a human or an animal or can transmit an electric signal for commanding the movement of a human body or the like to the inside of a living body, and can communicate information on the electric signal which is detected or to be transmitted with an external device.

BACKGROUND ART

In recent years, patients with Alzheimer's disease (one type of senile dementia) or a psychological disorder have been increased. For the patients, a means for operating various devices to be controlled (for example, a word processor or a vehicle unit) using a brain wave signal has been explored (for example, refer to Non-Patent Document 1 and Patent Document 1).

Non-Patent Document

Lakshmi Sandhana (Japanese edition by Mutsumi Hase/Ikuya Takamori), "Directly coupled brain and computer, new interface capable of handling wheelchair by just thinking", "online", Jul. 30, 2003, WIRED NEWS, "search for Jul. 8, 2004", Internet <URL: "http://hotwired.goo.ne.jp/news/technology/story/20030801301.html">

Patent Document 1

Japanese Patent Laid-Open No. 2004-152002

DISCLOSURE OF INVENTION

However, it is convenient that communication between a brain wave signal and an external device is carried out without wires (wireless) to offer convenience by a control means using the brain wave signal. In addition, the active performance of a user itself can be supported in the case of employing not a device to be controlled such as an electronic device or a mobile object as the external device but a memory capable of communicating without wires (wireless memory), in which a command on the movement of a human body is memorized. This means is significant for not only people who have diseases but also people who have no diseases.

The present invention is made to pursue such the convenience, and it is an object of the present invention to provide a biological signal processing unit which can detect a biological signal (typically, an electronic signal of a brain wave) from a human or an animal or can transmit an electronic signal for a command of the movement of a human body or the like, and can communicate information on the electronic signal which is detected or to be transmitted with an external device. Moreover, it is another object of the invention to provide a wireless memory capable of communicating with the biological signal processing unit, and a communication system between the biological signal processing unit and an external device such as an electronic device.

(1) A biological signal processing unit related to the invention has a feature of providing an electrode and an interface for detecting a biological signal (electric signal) from the inside of a living body or for transmitting an electric signal to the inside of a living body, and an antenna which can communicate with an external device.

The biological signal processing unit related to the invention serves as a biological signal sensor by being provided with the electrode for detecting a biological signal (electric signal). The number of the electrodes is not limited in particular; however, the electrode may be normally a multipoint electrode. Typically, there are a type of touching the surface of skin or the like and a type of directly sticking as an usage type of an electrode; however, any of the types can be employed. Such electrode is not limited, however the electrode disclosed in the U.S. Patent Application Publication No. 2005/0113744 A1 may be used as the electrode, for example. The entire contents of this publication are hereby incorporated by reference.

Here, the external device indicates a wireless memory, a reader/writer, or the like. In addition, the external device may be connected to an electronic device or the like. The reader/writer may have a function of at least any one of a reader and a writer.

The biological signal which is detected and controlled includes not only the biological signal of a human but also that of an animal. Typically, the biological signal means a brain wave, an electric signal transmitted to a brain, or a pulse.

A personal belonging such as a helmet, a hat, a pair of glasses, or a headphone, or an accessory or the like may have the built-in biological signal processing unit.

(2) A wireless memory related to the invention has a feature of being provided with a memory element which memorizes information on an electric signal transmitted to the inside of a living body, and an antenna.

The wireless memory indicates a memory which can communicate with an external terminal device (biological signal processing unit, reader/writer, or the like related to the invention) without wires through the antenna included in the wireless memory. There is no limitation on the kind of the memory; however, a ROM, a RAM, a nonvolatile memory (EPROM, EEPROM, UV-EPROM, flash memory, ferroelectric memory, or the like) can be typically used for the memory.

The wireless memory can be easily pasted to a human body or the like and exchanged, moreover information can be updated by an external device such as a reader/writer.

(3) A biological signal processing system related to the invention has a feature of including a biological signal processing unit provided with an electrode and an interface for transmitting an electric signal to the inside of a living body, and an antenna which can communicate with a wireless memory of the outside of a living body; and a wireless memory provided with a memory element which memorizes information on an electric signal transmitted to the inside of a living body, and an antenna which can communicate with the biological signal processing unit.

According to the invention, the biological signal processing unit related to the invention is made to be further accompanied with the wireless memory to carry communication without wires, and thus, new information which is not memorized in the biological signal processing unit can be transmitted to the inside of a living body as needed.

(4) A control system of a device to be controlled related to the invention has a feature of including a biological signal detecting unit provided with an electrode and an interface for detecting an electric signal from the inside of a living body, and an antenna which can communicate with a reader/writer outside of a living body; a reader/writer which can communicate with the biological signal detecting unit; and a device to be controlled connected to the reader/writer, and the device to be controlled can be controlled based on the electric signal from the inside of the living body, which is transmitted to the device to be controlled through the reader/writer.

An electronic device such as a personal computer, a mobile object such as a passenger car or a wheelchair can be typically given as the device to be controlled herein described; however, the device to be controlled is not limited thereto.

The reader/writer may be provided to be independent from the device to be controlled or may be mounted on the device to be controlled.

The biological signal processing unit related to the invention can communicate with the external device such as the wireless memory or the reader/writer without wires; therefore, the convenience of a user can be improved in the case where an electronic device or the like is remotely operated based on information on a biological signal (for example, a brain wave) of a user, or in the case where information related to a command of the movement of a human body memorized in the wireless memory is transmitted to the inside of a living body.

In addition, the wireless memory can be exchanged and rewritten according to need; therefore, information according to the disease condition or the desire of a user or the like can be provided.

Further, information on a command based on a biological signal of a user can be transmitted from the biological signal processing unit to the device to be controlled such as an electronic device or a mobile object through the wireless memory or the reader/writer described above; therefore, the device to be controlled can be remotely operated.

The biological signal processing unit and wireless memory are desirably formed using a thin film active element such as a thin film transistor (TFT) or the like. According to this, biological signal processing units and wireless memories which are smaller and thinner can be provided to be easily embedded in various commodities such as a helmet and a pair of glasses, pasted to the users, or carried by the user.

A biological signal processing unit and a wireless memory using a TFT can be produced in large amounts and at low cost by a method for carrying out an element separation by chemically and/or physically peeling a substrate to be peeled to perform element separation after forming a TFT included in the biological signal processing unit and the wireless memory over the substrate to be peeled. Therefore, back-grinding is not required unlike a conventional IC chip formed over a silicon substrate, and thus, the process can be substantially simplified and the manufacturing cost can be substantially reduced. In addition, a substrate which is more inexpensive than a silicon substrate, such as a glass substrate, a quartz substrate, or a solar battery grade silicon substrate can be used for the substrate to be peeled and further the substrate to be peeled can be reused; therefore, the cost can be drastically reduced. Further, the back-grinding treatment which causes a crack and a polished trace is not required to be performed unlike an IC manufactured by a silicon wafer. Moreover, variations in thickness of elements are dependent upon variations at the time of depositing each film which forms the biological signal processing unit and the wireless memory using the TFT; therefore, the variation is several hundreds nm at most, which is far less than the variations of several to several tens μm after the back-grinding treatment.

BRIEF DESCRIPTION OF DRAWINGS

In the accompanying drawings:

FIG. 2 is a block diagram showing a configuration of an electronic device control system related to the invention;

FIGS. 7A to 7C are views of a manufacturing step of a TFT used for a biological signal processing unit or a wireless memory related to the invention;

FIGS. 8A to 8C are views of a manufacturing step of a TFT used for a biological signal processing unit or a wireless memory related to the invention;

FIGS. 9A and 9B are views of a manufacturing step of a TFT used for a biological signal processing unit or a wireless memory related to the invention;

BEST MODE FOR CARRYING OUT THE INVENTION

Hereinafter, embodiments according to the present invention are described with reference to the drawings. However, it is easily understood by those who are skilled in the art that embodiments and details herein disclosed can be modified in various ways without departing from the purpose and the scope of the present invention. For example, any of the embodiments and examples can be appropriately combined to implement the present invention. Therefore, it should be noted that the description of embodiments to be given below should not be interpreted as limiting the present invention.
(Embodiment 1)

Figure 1:
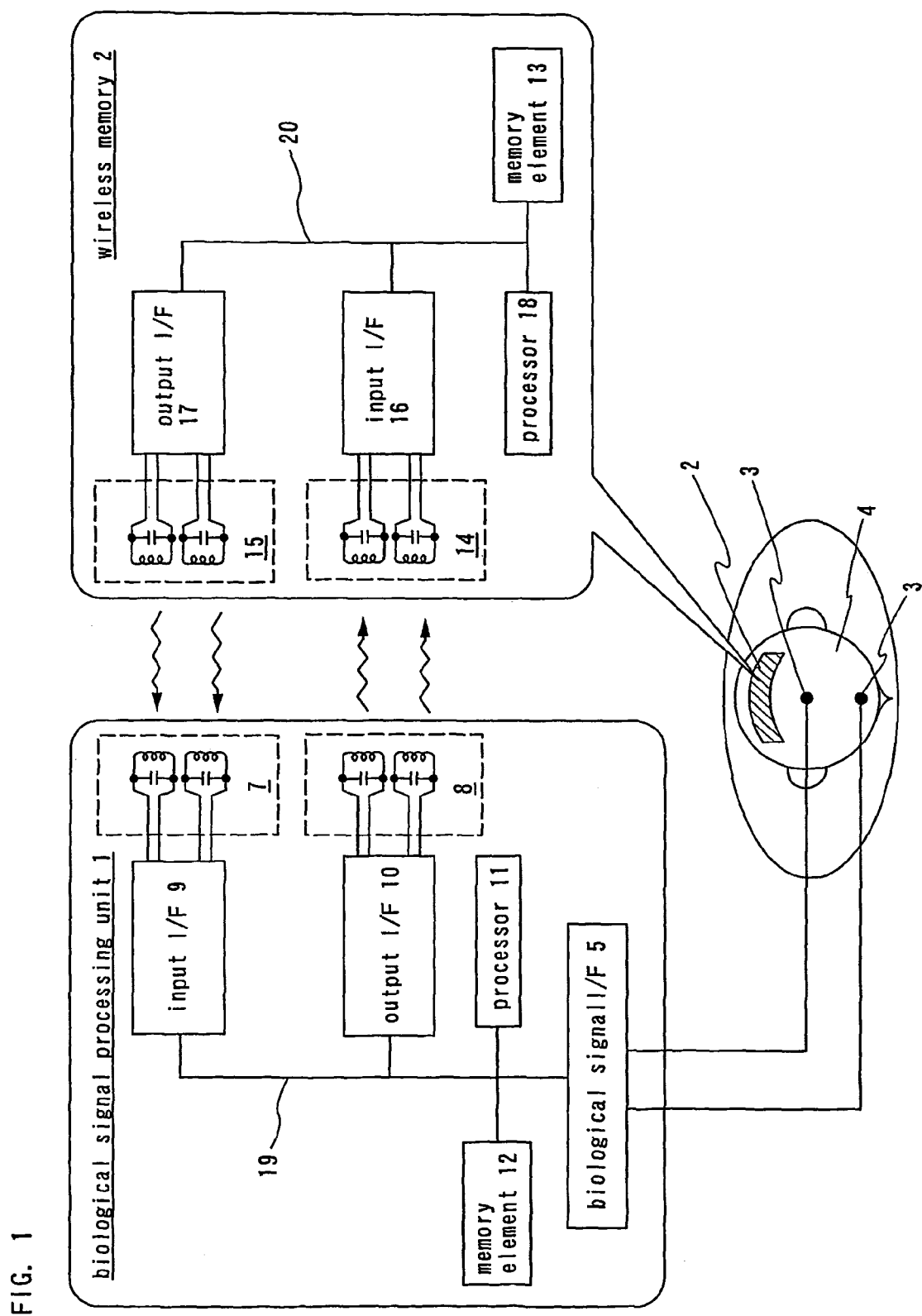
FIG. 1 is a block diagram showing a configuration of a biological signal-processing unit, a wireless memory, and a biological signal processing system related to the present invention.

A configuration of a biological signal processing unit 1 related to the invention is described with reference to FIG. 1. FIG. 1 shows a block diagram of the biological signal processing unit 1 and a block diagram of a wireless memory 2 which can communicate with the biological signal processing unit 1.

The biological signal processing unit 1 is provided with a plurality of electrodes 3 for detecting an electric signal of a brain wave of a human or an animal, or for transmitting an electric signal into the brain thereof, and the electrode 3 is used with being adhered to a head 4 (scalp) of a human and an animal. The electrode 3 is desirably adhered to any of the positions from a frontal lobe to a vertex; however, the position is not necessarily limited to this. Also, the number of the electrodes 3 is not limited to the number which is shown.

The biological signal processing unit 1 and the electrode 3 are separated in FIGS. 1 to 3C; however, the electrode 3 is included in the biological signal processing unit 1.

The biological signal processing unit 1 is provided with a processor 11 for processing the brain wave detected by electrode 3. The processor 11 performs signal processing such as amplification, level adjustment, or digital/analog conversion, and various control processings.

Further, the biological signal processing unit 1 is provided with a biological signal interface (hereinafter, referred to as a "biological signal I/F 5") between the electrode 3 and the processor 11, or between the electrode 3 and antennas 7 and 8. The biological signal I/F 5 may serve as a wiring for transmitting a brain wave (including a brain wave converted to an electric signal) detected by the electrode 3, and may be an element having a function similar to the above described processor 11 as shown in FIGS. 1 to 3C. For example, in the case where an electric signal is transmitted into the brain through the electrode 3, the biological signal I/F 5 carries out the function of converting the electric signal to an appropriate brain wave.

The biological signal I/F 5 may be provided by being separately divided into an output (detection) portion of a biological signal I/F and an input (transmission) portion of a biological signal I/F. Alternatively, the output portion of the biological signal I/F and the input portion of the biological signal I/F may be integrated with each other.

The biological signal processing unit 1 is provided with antennas 7 and 8 for communicating information based on the detected brain wave signal to an external device such as the wireless memory 2 or a reader/writer hereinafter, referred to as a "R/W 6") as shown in FIG. 2 without wires. The antennas may be separately divided into an input antenna and an output antenna as shown, or may be provided to be integrated. An input interface (hereinafter, referred to as an "input I/F 9") is provided corresponding to the input antenna 7, and an output interface (hereinafter, referred to as an "output I/F 10") is provided corresponding to the output antenna 8 in FIG. 1; however, both of the interfaces may be formed to be integrated or may be formed to be integrated with the biological signal I/F 5.

Here, the input I/F 9 of the input antenna 7 is generally provided with a demodulation circuit. In the case where the biological signal processing unit 1 is a so-called passive type driven by an electric power supply from an outside, the input I/F 9 is provided with a rectification circuit. In other words, alternating current power supply voltage inputted from the input antenna 7 is rectified at the rectification circuit and supplied to the various circuits described above as direct current power supply voltage. In addition, various alternating current signals inputted from the input antenna 7 are demodulated at the demodulation circuit. Then, the various signals shaped in waveforms by the demodulation are supplied to the various circuits.

On the other hand, the output I/F 10 of the output antenna 8 is generally provided with a modulation circuit and an amplifier. In other words, the various signals inputted to the output I/F 10 are modulated at the modulation circuit, and amplified, or buffered and amplified at the amplifier, then, sent from the output antenna 8 to an external terminal device such as the wireless memory 2 or the reader/writer.

The material of the antenna is not especially limited when the material has conductivity; however, for example, Ag, Au, Al, Cu, Zn, Sn, Ni, Cr, Fe, Co, or Ti, or an alloy including the same can be used. Conductive polymer may be used without being limited to metal. The antenna preferably has a film thickness of from 5 μm to 60 μm.

In addition, the number of various antennas is not limited to the number thereof shown in FIG. 1. Further, the shape of the antenna is not limited to a coil shape.

Arithmetic processing of the detected brain wave signal may be performed by a processor 11 according to need. A processor which is typical as the processor 11 is a CPU or a MPU. At this time, a coprocessor for serving as an auxiliary processor which supports the operation of the processor 11 may be separately provided.

In addition, information on the detected brain wave signal or information to be transmitted to a brain as a brain wave can be stored in a memory element 12. Typically, a ROM, a RAM, a nonvolatile memory (EPROM, EEPROM, UV-EPROM, flash memory, ferroelectric memory, or the like) can be used for a memory included in the memory element 12.

The various interfaces and antennas, the processor 11, and the memory element 12 are connected through a bus line 19.

The above is a configuration of the biological signal processing unit 1 related to the invention, and according to this, information based on the detected brain wave signal can be communicated with the external device such as the wireless memory 2 or the reader/writer without wires. On the other hand, information inputted from the external device such as the wireless memory 2 or the reader/writer is converted into a brain wave signal which is to be transmitted to the brain by the various interfaces, and then, transmitted to the brain through the electrode 3.

The biological signal processing unit related to the invention can communicate with the external device such as the wireless memory or the reader/writer without wires; therefore, convenience of a user can be improved in the case where an electronic device or the like is remotely operated based on information on the brain wave of the user such as a patient, or in the case where information related to a command of the movement of a human body memorized in the wireless memory is transmitted to the brain.

(Embodiment 2)

In this embodiment, a configuration of a wireless memory 2 which can communicate with a biological signal processing unit 1 related to the present invention and a communication method between the biological signal processing unit 1 and the wireless memory 2 are described with reference to FIG. 1.

The wireless memory 2 related to the invention includes at least a memory element 13, antennas 14 and 15 which communicate with the biological signal processing unit 1 as shown, and further includes an input I/F 16, an output I/F 17, a processor 18, a coprocessor (not shown) which supports the processor, and the like according to need, and they are connected with each other through a bus line 20. An object which is typical as the processor 18 is a CPU or a MPU.

Here, information which is to be transmitted to a brain as a brain wave is mainly stored in the memory element 13. Typically, a ROM, a RAM, a nonvolatile memory (EPROM, EEPROM, UV-EPROM, flash memory, ferroelectric memory, or the like) can be used for a memory included in the memory element 13.

The information memorized in the memory element 13 is demodulated into a signal which can be communicated by the output I/F 17, then, sent to the biological signal processing unit 1 by the output antenna 15.

Here, the wireless memory 2 mainly has a purpose of memorizing information supplied to a brain as a brain wave. Therefore, the input antenna 14 and the input I/F 16 are not required; however, the input antenna 14 and the input I/F 16 may be provided in the case where a memory element 12 is not provided for the biological signal processing unit 1, or in the case where information based on a detected-brain wave is stored in the wireless memory 2 in addition to the memory element 12. In this case, the input I/F 16 mainly has a purpose of demodulating a signal received from the biological signal processing unit 1.

In the case of providing the processor 18 for the wireless memory 2, the wireless memory can be considered to be a wireless processor or a wireless memory processor. However, the wireless memory 2 mainly has a purpose of memorizing information supplied to a brain as a brain wave in this embodiment; therefore, it is referred to as the wireless memory 2 even in the case of incorporating a processor.

The wireless memory 2 is desirably formed over a flexible substrate to be able to be easily pasted to a head 4 of a human or an animal, a part of a human body, or the like (refer to FIG. 1).

Thus, according to the wireless memory 2, a command required for the movement of a human body can be transmitted by supplying information required for a brain as a brain wave. For example, the wireless memory plays a role which supports the daily life of a patient with Alzheimer's disease. Information which commands a movement required for the daily life of a human or the like is memorized in the wireless memory 2, and the wireless memory 2 can be easily replaced or the information can be rewritten from the outside by the R/W according to the level of the symptom of a patient.

The position of pasting the wireless memory 2 can be appropriately selected according to a positional relation of the antenna included in the biological signal processing unit 1 or a communication method between the wireless memory 2 and the biological signal processing unit 1.

Here, the following method can be typically used as the communication method: an electromagnetic induction type utilizing induced electromotive force (a communication distance of approximately 1 m or less), an electromagnetic coupling type utilizing mutual induction of a coil due to an alternating current magnetic field or an electrostatic coupling type utilizing an inductive action due to static electricity (each communication distance of approximately several mm to several ten mm), a microwave type for sending and receiving data utilizing a microwave (2.45 GHz) (a communication distance of approximately several m), or an optical communication type for updating information of an ID label by utilizing space electrical transmission by light utilizing near-infrared ray (a communication distance of approximately several ten cm).

For example, in the case where the wireless memory 2 is pasted to a head, an electromagnetic coupling type or an electrostatic coupling type which has a short communication distance may be employed.

The material, the shape, or the like of the antenna in the wireless memory 2 is based on Embodiment 1.

A method for supplying electric power to the biological signal processing unit 1 in this embodiment may be a so-called passive type in which electric power supply voltage is supplied from the wireless memory 2 which is an external terminal device or may be a so-called active type in which the biological signal processing unit 1 itself has an original battery.

A biological signal processing system which can command to the movement of a human body or the like can be obtained by combining the biological signal processing unit 1 related to Embodiment 1 and the wireless memory 2 related to this embodiment. The biological signal processing system can support the daily life of a patient especially with a brain disorder.

The wireless memory can be exchanged and be rewritten according to need; therefore, information according to the desire of a user can be provided.

(Embodiment 3)

An electronic device control system related to the present invention is described with reference to FIG. 2. FIG. 2 is a block diagram showing a configuration of the electronic device control system related to the invention. A configuration of a biological signal processing unit 1 in FIG. 2 is based on that of Embodiment 1.

The electronic device control system includes a R/W 6 and an electronic device 26 which is to be controlled, in addition to the biological signal processing unit 1. The mechanism of the R/W 6 may be provided so as to be separated from the electronic device 26 or may be mounted on the electronic device 26.

Here, the R/W 6 includes at least an input antenna 21, an input I/F 23, an output antenna 22, an output I/F 24, and a control section 25 for data processing. However, there is no limitation thereon, in the case where the R/W 6 has only a reading (input) function and a writing (output) function is not required. The material, the shape, or the like of the antenna is based on Embodiment 1.

The input I/F 23 mainly has a purpose of demodulating a signal received from the biological signal processing unit 1 so that data processing can be carried out in the control section 25. On the other hand, the output I/F 24 mainly has a purpose of modulating and amplifying information from the control section 25 into a signal which can be communicated.

The R/W 6 is connected to various electronic devices 26 to be able to remotely operate the electronic device 26 based on information on a brain wave detected by the biological signal processing unit 1. The distance which allows the remote operation is determined by a method for communicating between the biological signal processing unit 1 and the R/W 6. The communication method is based on Embodiment 2.

A command for the electronic device 26 corresponding to the detected brain wave may be read by installing software 27 in advance.

A personal computer, a household audio equipment such as a TV set, a radio, a CD player, a MD player, a cassette tape deck, or a DVD player, a mobile device such as a cellular phone or a PDA, or the like can be typically given as the electronic device 26 described herein; however, the electronic device is not limited thereto if the electronic device can command the movement by converting a brain wave into an electric signal.

Information obtained by the electronic device 26 can be made to be fed back to the brain as a brain wave through the R/W 6 and the biological signal processing unit 1.

The system related to this embodiment can be employed for a mobile object such as a car, or other devices to be controlled, in addition to an electronic device. The mobile object includes a wheelchair for a disabled person or the like.

The invention related to this embodiment can be implemented by interposing the wireless memory 2 in Embodiment 2 between the biological signal processing unit 1 and the R/W 6. In this case, wireless communication is performed between the wireless memory 2 and the R/W 6.

A method for supplying electric power to the biological signal processing unit 1 in this embodiment may be a so-called passive type in which electric power supply voltage is supplied from the R/W 6 which is an external terminal device or may be a so-called active type in which the biological signal processing unit 1 itself has an original battery.

EXAMPLE 1

Figure 3A:
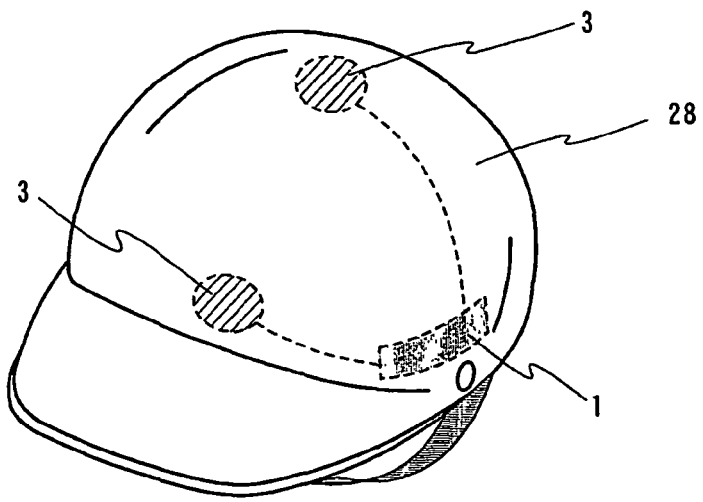
FIGS. 3A to 3C are views showing one example of a commodity having a biological signal processing unit related to the invention.
Figure 3B:
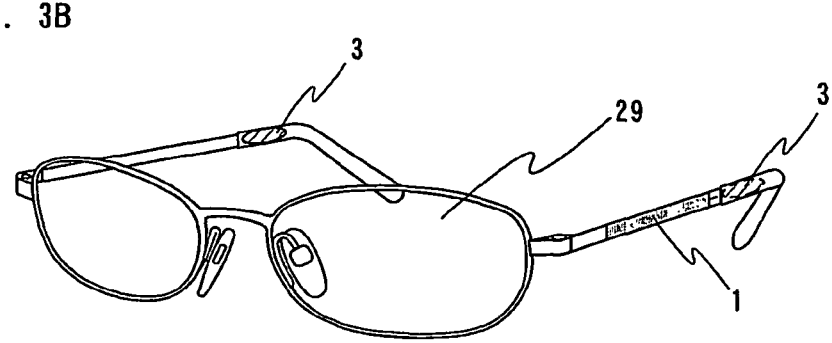
Figure 3C:
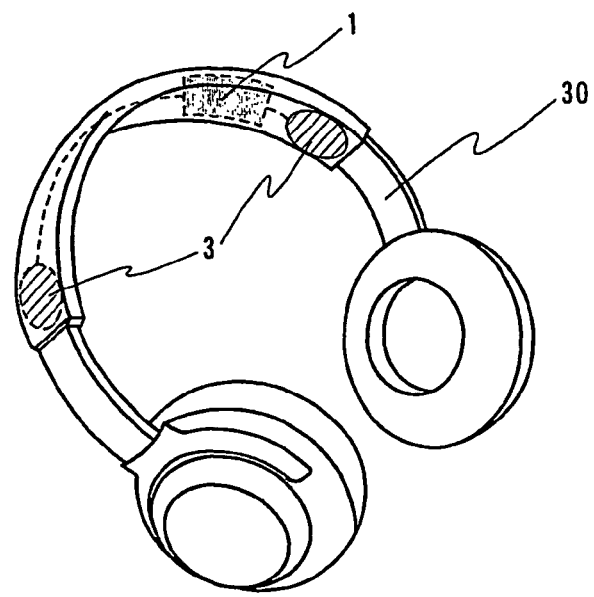

In this example, one example of a commodity having a biological signal processing unit 1 shown in Embodiment 1 is shown with reference to FIGS. 3A to 3C. FIG. 3A shows a helmet 28 with the built-in biological signal processing unit 1 (including an electrode 3) related to the invention, FIG. 3B shows a pair of glasses 29 with the built-in biological signal processing unit 1 (including an electrode 3) related to the invention, and FIG. 3C shows a headphone 30 with the built-in biological signal processing unit 1 (including an electrode 3) related to the invention.

The electrode 3 for being adhered to a head is provided in any of the commodities. The position and the number of the electrodes 3 are not limited to those of the objects shown in the figures. The mode of each commodity is also not limited to those of the objects shown in the figures. A peculiar mode due to the adjustment of a position provided with the electrode 3 may be employed. The electrode 3 is connected to an interface or the like in the biological signal processing unit 1 through a wiring.

An object capable of applying the biological signal processing unit 1 related to the invention is not limited to a commodity related to this example, and can be applied to a commodity which can be adhered to a head such as a hat or an accessory.

EXAMPLE 2

Figure 4:
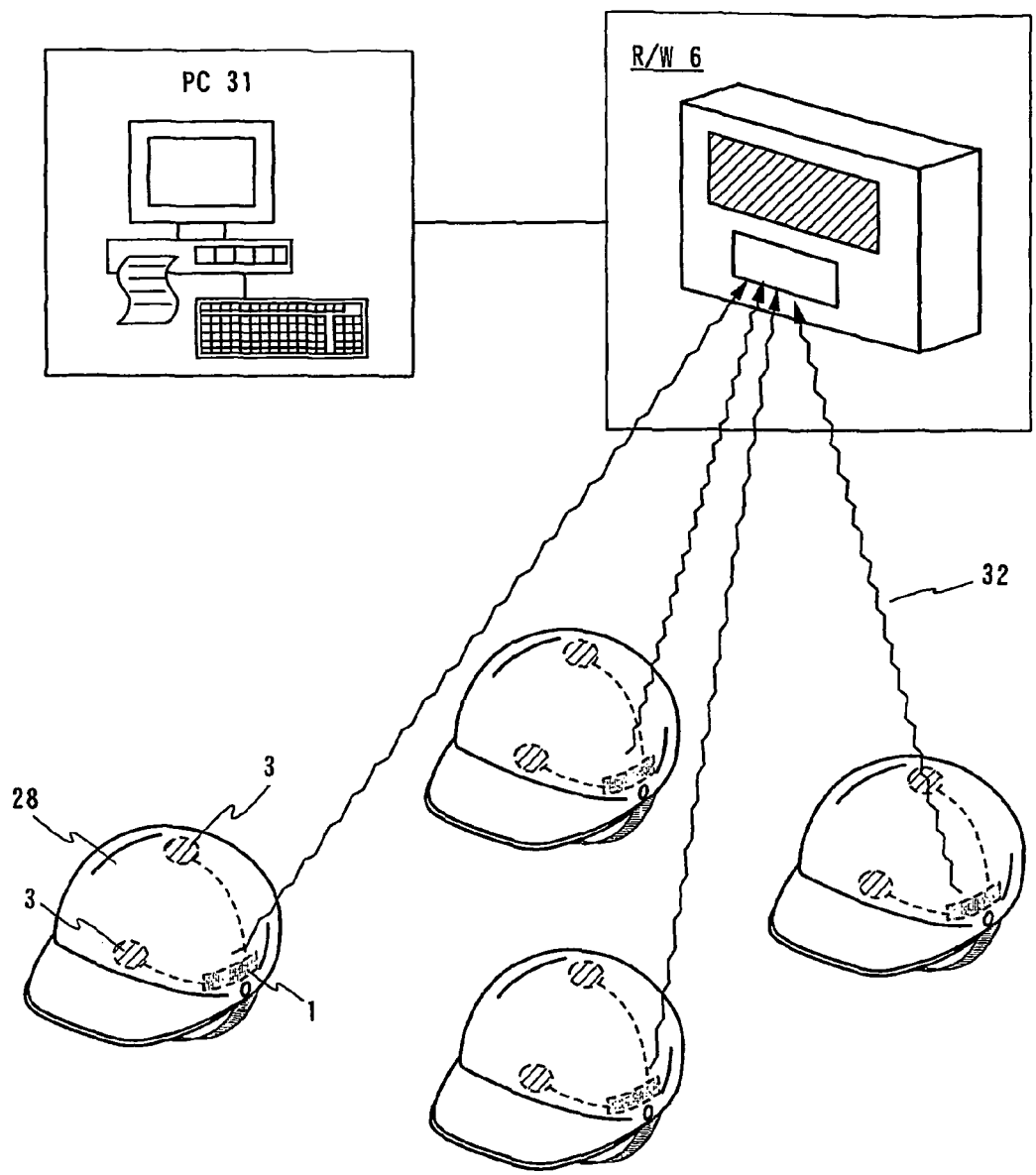
FIG. 4 is an explanatory view of an example using a biological signal processing unit system related to the invention.

In this example, a system for carrying out health management of a worker in a construction field using a helmet related to Example 1 is described with reference to FIG. 4. FIG. 4 shows a schematic view of a health management system for a worker.

Each worker wears a helmet 28 with a built-in biological signal processing unit 1, therefore information on a brain wave detected by the biological signal processing unit 1 can be read by a R/W 6. Information between the biological signal processing unit 1 and the R/W 6 can be generally exchanged using an electromagnetic wave 32. Then, data processing of the information on the brain wave of each worker read by the R/W 6 is performed by using a personal computer (PC 31) or the like. Thus, health condition or the like of each worker can be grasped.

The health management system related to the invention is significant especially in the case of concerning the life of a worker, for example, a work of handling a hazardous material, a work under the ground or rare air condition, or a work in a nuclear power station.

A communication method shown in Embodiment 2 can be employed; however, a method having a communication distance as long as possible is desirably employed.

EXAMPLE 3

In this example, a manufacturing step of an integrated circuit by a stress peel off process in the case of using a TFT as an element included in the integrated circuit, such as a memory element or a processor in a biological signal processing unit 1 or in a wireless memory 2 related to the present invention, is described.

Figure 5A:
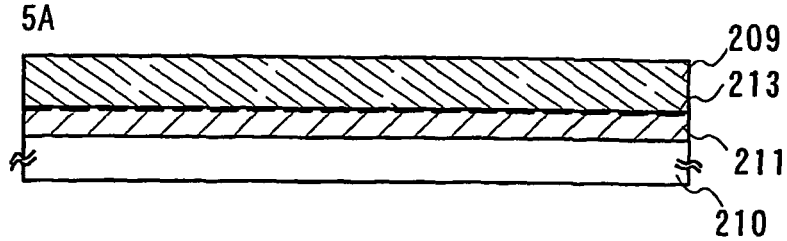
FIGS. 5A to 5E are views of a manufacturing step of a biological signal processing unit or a wireless memory related to the invention.

First, as shown in FIG. 5A, a metal film 211 is formed over a first substrate 210 having an insulating surface. The first substrate may have rigidity capable of withstanding a subsequent peeling step. For example, a glass substrate, a quartz substrate, a ceramic substrate, a silicon substrate, a metal substrate, or a stainless steel substrate can be used as the first substrate. A single layer formed from an element selected from W, Ti, Ta, Mo, Nd, Ni, Co, Zr, Zn, Ru, Rh, Pd, Os, and Ir, or an alloy material or a compound material containing the element as its main component; or a lamination of the single layers can be used as the metal film. As a method for manufacturing the metal film, for example, a sputtering method using a metal target may be used. The metal film may be formed to have a film thickness of from 10 nm to 200 nm, preferably from 50 nm to 75 nm.

A metal nitride film formed from the above metal (for example, tungsten nitride or molybdenum nitride) may be used instead of the metal film. In addition, a film formed from an alloy of the above metal (for example, an alloy of W and Mo:$W_xMo_{1-x}$) may be used instead of the metal film. In this case, a sputtering method using a plurality of targets of a first metal (W) and a second metal (Mo) or using a target of the alloy of a first metal (W) and a second metal (Mo) in a deposition chamber may be used. Further, nitrogen or oxygen may be added to the metal film. For an example of a method for adding oxygen or nitrogen, oxygen or nitrogen ion implantation, or sputtering under nitrogen or oxygen atmosphere in a film formation chamber can be given. In the latter case, a metal nitride may be used as a target.

A peeling step can be simplified by appropriately setting a material or a method for forming the metal film. For example, heat treatment can be omitted in the case of using Mo as the metal film.

Subsequently, a layer to be peeled 209 having an element formation region is formed over the metal film 211. This layer to be peeled is formed by stacking an oxide film containing silicon so as to be in contact with the metal film. The layer to be peeled may have an antenna. The layer to be peeled 209 is preferably provided with an insulating film containing nitrogen such as a silicon nitride (SiN) film or a silicon nitride oxide (SiON or SiNO) film so that the insulating film containing nitrogen is in contact with the metal film to prevent the penetration of impurities or dust from the metal film or the substrate. The insulating film serves as a base film of the thin film transistor.

Silicon oxide, silicon oxynitride, or the like may be formed as the oxide film containing silicon by a sputtering method or a CVD method. It is desirable that a film thickness of the oxide film containing silicon is approximately twice or more as thick as the metal film. In this example, a silicon oxide film is formed so as to have a film thickness of from 150 nm to 200 nm by a sputtering method using a silicon target.

When the oxide film containing silicon is formed, a metal oxide film 213 containing the metal is formed over the metal film. A thin metal oxide film formed over the surface of the metal film by treating with an aqueous solution containing sulfuric acid, hydrochloric acid, or nitric acid; an aqueous solution in which hydrogen peroxide water is mixed with sulfuric acid, hydrochloric acid, or nitric acid; or ozone water can be used as the metal oxide film. Further, plasma treatment in an oxygen atmosphere or oxidation treatment with ozone generated by ultraviolet irradiation in an atmosphere containing oxygen may be carried out as other methods. Furthermore, the metal oxide film may be formed by heating at a temperature of from 200° C. to 350° C. with a clean oven.

The metal oxide film may be formed to have a film thickness of from 0.1 nm to 1 μm, preferably from 0.1 nm to 100 nm, and more preferably from 0.1 nm to 5 nm.

The oxide film containing silicon, the base film, or the like is collectively referred to as an insulating film. In other words, the metal film, the metal oxide film, the insulating film, and a semiconductor film are stacked. In addition, the metal film and the metal oxide film can be referred to as a peeling layer.

A predetermined manufacturing step is performed on the semiconductor film to form a thin film transistor (TFT) in which at least a channel formation region is formed from an island-shaped separated semiconductor film having a film thickness of from 10 nm to 200 nm. This semiconductor element is included in an integrated circuit such as a memory element 13, a processor 18, and various interfaces. An insulating film containing carbon such as DLC or carbon nitride (CN) or an insulating film containing nitrogen such as silicon nitride (SiN) or silicon nitride oxide (SiNO or SiON) is preferably provided over the semiconductor element as a protective film which protects the semiconductor element.

After forming the above-mentioned layer to be peeled 209, specifically, after forming the metal oxide film, heat treatment is appropriately carried out to crystallize the metal oxide film. For example, in the case of using W (tungsten) for the metal film, the metal oxide film of $WO_x$ (x=2 to 3) comes into a crystal condition when heat treatment is carried out at a temperature of 400° C. or more. In such the heat treatment, a temperature or the necessity of the heat treatment may be determined according to the metal film to be selected. In other words, the metal oxide film may be crystallized according to need to peel easily.

In the case where heating is performed after forming the semiconductor film of the layer to be peeled 209, hydrogen in the semiconductor film can be diffused. There is a case that valence of the metal oxide film varies due to this hydrogen.

Further, the number of steps for manufacturing the semiconductor element may be reduced by using the heating treatment both as a manufacturing step of a semiconductor element and a heating step. For example, heat treatment can be performed using a heating furnace or laser irradiation used in the case of forming a crystalline semiconductor film.

Figure 5B:
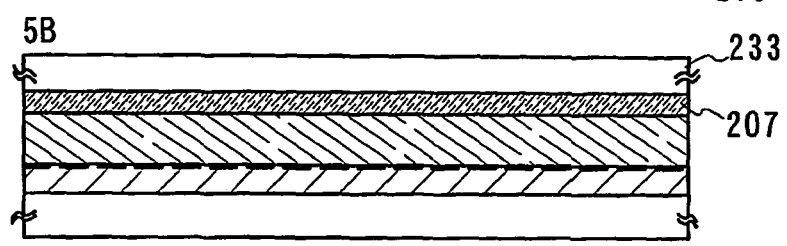

Then, as shown in FIG. 5B, the layer to be peeled 209 is pasted to a support substrate 233 with a first adhesive agent 207. A substrate having higher rigidity than that of the first substrate 210 is preferably used for the support substrate 233. An adhesive agent which can be peeled, for example, an ultraviolet peeling type adhesive agent which is peeled by ultraviolet, a heat peeling type adhesive agent which is peeled by heat, or a water-soluble adhesive agent which is peeled by water; a two-sided tape; or the like may be used for the first adhesive agent 207.

Figure 5C:
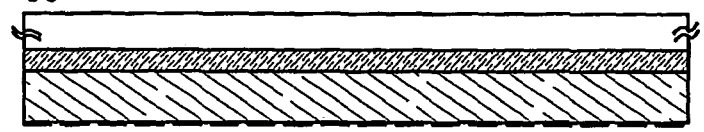

Then, the first substrate 210 provided with the metal film 211 is peeled by a physical means (FIG. 5C). The first substrate is separated within layers of the crystallized metal oxide film, or at an interface between the metal oxide film and the metal film or at an interface between the metal oxide film and the layer to be peeled although it is not illustrated in the figure since it is a schematic view. Thus, the layer to be peeled 209 can be peeled from the first substrate 210. The first substrate is separated from any one of the interfaces. Thus, the layer to be peeled 209 can be peeled from the first substrate 210.

At this time, it is preferably that a part of the substrate is cut to scratch the vicinity of a peeling interface at the cut surface, namely the interface of the metal film and the metal oxide film with a cutter or the like in order to perform the peeling easily.

Figure 5D:
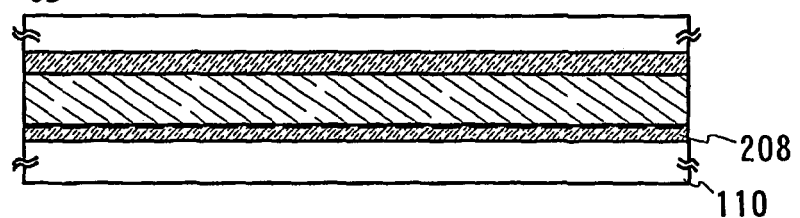

And then, as shown in FIG. 5D, the layer to be peeled 209 which is peeled is pasted and fixed to a second substrate 110 (for example, a flexible substrate such as a plastic substrate), which is to be a transcriptional body, with a second adhesive agent 208. In the case where an antenna is provided for the layer to be peeled 209, the element formation region and the antenna are simultaneously fixed to the second substrate. An ultraviolet curable resin, specifically, an epoxy resin adhesive agent or an adhesive agent such as a resin additive, a two-sided tape, or the like may be used for the second adhesive agent 208. In the case where the second substrate 110 has an adhesive property, the second adhesive agent is not required.

As the second substrate 110, a plastic material or the like such as polyethylene terephthalate, polycarbonate, polyarylate, polyethersulfone, or the like can be used. Such the second substrate is referred to as a plastic substrate. Such the plastic substrate has flexibility and lightweight. Irregularity of the surface may be reduced, and rigidity, resistance characteristics, and stability may be enhanced by performing coating treatment on the plastic substrate.

Figure 5E:

Then, the first adhesive agent 207 is removed to peel the support substrate 233 (FIG. 5E). Specifically, the first adhesive agent may be peeled by ultraviolet irradiation, heating, or washing.

Further, removing the first adhesive agent 207 and curing the second adhesive agent 208 may be carried out in one process. For example, in the case where a pair of a heat peeling type resin and a thermosetting resin, or a pair of an ultraviolet peeling type resin and an ultraviolet curing type resin are used for a pair of the first adhesive agent 207 and the second adhesive agent 208, respectively, the removing and curing can be carried out by once performing heating or ultraviolet irradiation.

The integrated circuit fixed to the plastic substrate can be formed as described above.

There is a case that the metal oxide film 213 is wholly removed from the integrated circuit or a case that a part or most of the metal oxide film 213 dots (remains in) the lower surface of the layer to be peeled. In the case where the metal oxide film 213 remains, the integrated circuit may be fixed to the flexible substrate such as a plastic substrate after removing the metal oxide film by etching or the like. In this case, the oxide film containing silicon may be removed.

The integrated circuit is formed using an island-shaped separated semiconductor film having a film thickness of from 10 nm to 200 nm, while a film thickness of an IC manufactured with a silicon wafer is approximately 50 µm; therefore, the integrated circuit becomes extremely thin. As a result, the biological signal processing unit or the wireless memory of the invention can be formed to be extremely thin, flexible, and lightweight. Consequently, the biological signal processing unit or the wireless memory which is superior in impact resistance characteristics and flexibility can be obtained.

Further, the back-grinding treatment that causes a crack and a polished trace is not required unlike an IC manufactured by a silicon wafer. Moreover, variations in thickness of elements are dependent upon variations of each film at the time of depositing the semiconductor film or the like; therefore, the variation is several hundreds nm at most, which is far less than the variations of several to several tens µm after the back-grinding treatment.

A substrate provided with an element formation region can be reused by a stress peel off process method as described above, and consequently, a manufacturing cost of a wireless processor or a biological signal processing unit can be reduced. Further, the substrate provided with the element formation region is not required to transmit laser light; therefore, the degree of freedom of design can be increased.

EXAMPLE 4

In this example, a method for fixing an element formation region of a wireless memory 2 to a flexible substrate by a different method from the above example is described. This example explains the wireless memory 2 as an example; however, a biological signal processing unit 1 can be similarly manufactured.

Figure 6A:
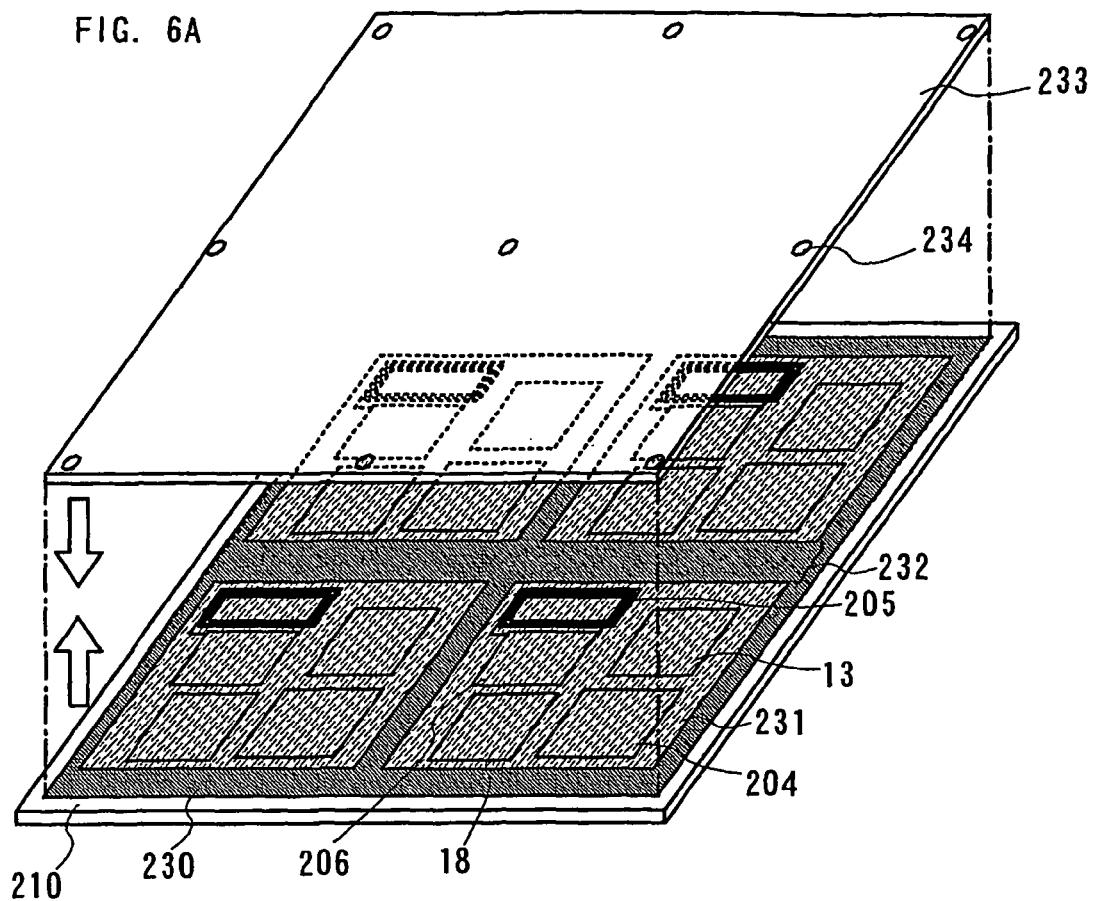
FIGS. 6A and 6B are views of a manufacturing step of a biological signal processing unit or a wireless memory related to the invention.

As shown in FIG. 6A, a peeling layer 230 and a layer to be peeled having an element formation region 231 are sequentially formed over a first substrate 210 which is an insulating substrate. The element formation region 231 has a processor 18, a memory element 13, an interface 204, an antenna 205, and a power supply circuit 206. A structure or a manufacturing method of the layer to be peeled having the element formation region 231 is the same as that of Example 3.

A film containing silicon or a metal film can be used for the peeling layer 230. The state of the film containing silicon may be any one of an amorphous semiconductor, a semi-amorphous semiconductor (also referred to as SAS) in which an amorphous state and a crystal state is mixed, and a crystalline semiconductor SAS includes a microcrystal semiconductor in which a crystal grain size of from 0.5 nm to 20 nm can be observed in an amorphous semiconductor. These peeling layers 230 can be formed by a sputtering method, a plasma CVD method, or the like. The peeling layer 230 may have a film thickness of from 0.03 μm to 1 μm, and the film thickness can be 0.03 μm or less if the thin film formation limit of a deposition apparatus of the peeling layer allows.

An element such as phosphorus or boron may be added to the peeling layer containing silicon. The element may be activated by heat or the like. The reaction speed of the peeling layer, namely an etching rate can be improved by adding the element.

As for the layer to be peeled, an insulating film is formed in a region being in contact with the peeling layer 230 so that the element formation region 231 is not etched. The insulating film can serve as a base film of a thin film transistor. A single layer structure of an insulating film containing oxygen or nitrogen such as silicon oxide (SiOx), silicon nitride (SiNx), silicon oxynitride (SiOxNy) (x>y), or silicon nitride oxide (SiNxOy) (x>y) (x, y=1, 2 . . . ), or a laminated structure thereof can be used for the insulating film. For example, in the case of using a laminated structure of three layers, a silicon oxide film can be used as a first insulating film; a silicon oxynitride film, as a second insulating film; and a silicon oxide film, as a third insulating film. The silicon oxynitride film is preferably used for these insulating films considering impurity diffusion from the first substrate 210 or the like; however, there is concern that the silicon oxynitride film has low adhesion with the peeling layer and a semiconductor film of a TFT. Therefore, a laminated structure of three layers provided with a silicon oxide film having high adhesion among the peeling layer, the semiconductor film, and the silicon oxynitride film may be used.

In this state, an opening 232 exposing the peeling layer 230 is formed outside of the element formation region 231. Then, the support substrate 233 provided with a hole 234 is fixed to the first substrate 210 with an adhesive agent. A resin material such as an ultraviolet curable resin or a thermosetting resin, or a two-sided tape, or the like can be used as the adhesive agent.

Figure 6B:
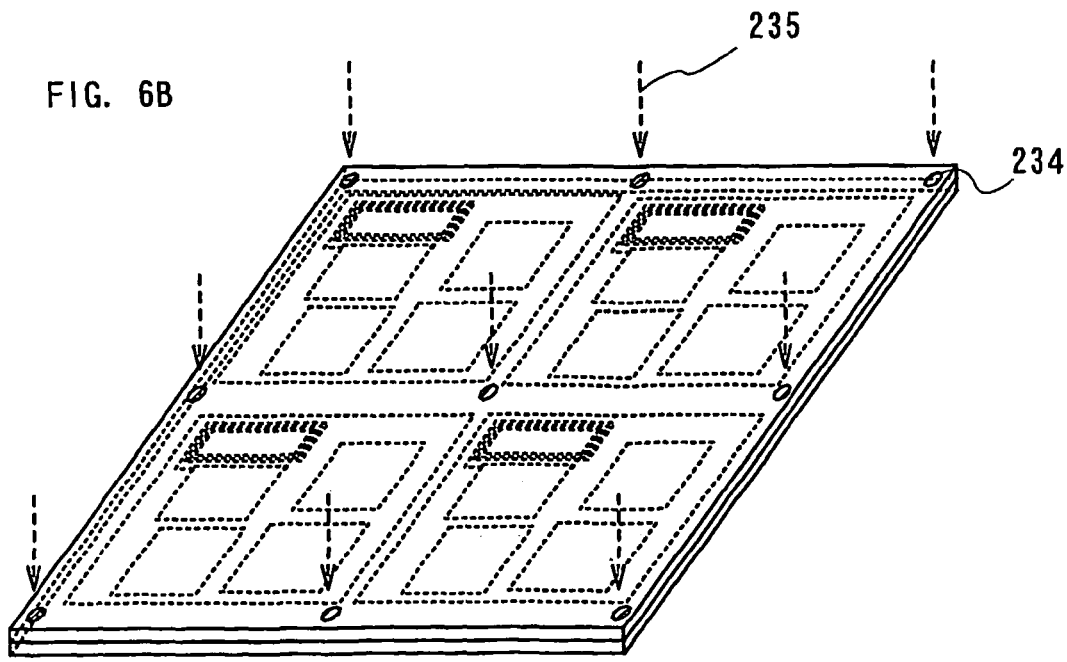

As shown in FIG. 6B, an etchant 235 (etching agent) is introduced into the opening 232 through the hole 234. Consequently, the peeling layer 230 can be removed. In the case of using a metal film as a peeling layer, the peeling layer can be removed by reacting at least the reactant with the etchant.

Gas or liquid containing halogen fluoride can be used as the etchant 235. For example, $ClF_3$ (chlorine trifluoride) can be used as halogen fluoride. The peeling layer 230 is selectively etched by introducing the etchant 235. More specifically, the peeling layer can be removed using a low pressure CVD apparatus in the following condition: a temperature is 350° C.; a flow of $ClF_3$ is 300 sccm; a pressure is 798 Pa (6 Torr); and time is 3 hours.

Thus, the peeling layer 230 is removed and the first substrate 210 is peeled. And then, the element formation region 231 can be fixed over the second substrate 110 having flexibility such as a plastic substrate or a plastic film substrate with an adhesive agent. A resin material such as an ultraviolet curable resin or a thermosetting resin, a two-sided tape, or the like can be used as the adhesive agent.

In the case of forming a wireless memory or a biological signal processing unit, the first substrate 210 can be reused. Consequently, a manufacturing cost of a wireless memory or the like can be reduced. Further, the substrate provided with the element formation region is not required to transmit laser light; therefore, the degree of freedom of design can be increased.

EXAMPLE 5

In this example, a method for fixing an element formation region to a flexible substrate using a different peeling layer from the above example and a manufacturing process of a thin film transistor are described with reference to FIGS. 7A through 9B.

In this example, metal is used for the peeling layer. A single layer formed from an element selected from W, Ni, Ta, Mo, Nd, Ni, Co, Zr, Zn, Ru, Rh, Pd, Os, and Ir, or an alloy material or a compound material containing the element as its main component; or a lamination of the single layers can be used for the metal used for the peeling layer.

The metal film can be formed by a sputtering method, a plasma CVD method, or the like. Specifically, the metal film may be formed over a first substrate using metal as a target in the case of using a sputtering method. The metal film is formed to have a film thickness of from 10 nm to 200 nm, preferably from 50 nm to 75 nm. A metal film which is nitrided (metal nitride film) may be used instead of the metal film. Further, nitrogen or oxygen may be added to the metal film. For example, the metal film may be formed by ion-implanting nitrogen or oxygen therein, or the metal film may be formed by a sputtering method in a nitrogen atmosphere or an oxygen atmosphere in a deposition chamber or the metal film may be formed by using a metal nitride target. At this time, in the case of using a mixture of the above metal (for example, an alloy of W and Mo:$W_{(x)}Mo_{(1-x)}$) for the metal film, the metal film may be formed by a sputtering method arranging a plurality of targets such as a first metal (W) and a second metal (Mo) or a target of the alloy of a first metal (W) and a second metal (Mo) in a deposition chamber.

Then, oxide, nitride, or nitride oxide containing the metal is formed over the metal film. The oxide, nitride, or nitride oxide containing the metal is collectively referred to as a reactant. For example, the oxide, nitride, or nitride oxide containing the metal becomes oxide, nitride, or nitride oxide of W or Mo, or a mixture of W and Mo in the case of using W, Mo, or a mixture of W and Mo.

Such the reactant is formed when a film containing oxide, nitride, or nitride oxide is formed over the metal film.

In this example, a silicon oxide film 212 is formed over a metal film 211 containing W. Then, a metal oxide film 213 which is an oxide film containing W, for example, $WO_x$ (x=2 to 3) is formed over the surface of the metal film 211 containing W. Similarly, a nitride film containing W may be formed when a silicon nitride film is formed over the metal film 211 containing W, and a nitride oxide film containing W may be formed when a silicon nitride oxide film is formed over the metal film 211 containing W.

A method for treating the metal film with an aqueous solution containing sulfuric acid, hydrochloric acid, or nitric acid, an aqueous solution in which hydrogen peroxide water is mixed with sulfuric acid, hydrochloric acid, or nitric acid, or ozone water may be used as a means for forming the above oxide among the reactants. Further, plasma treatment in an oxygen atmosphere or oxidation treatment which generates ozone by ultraviolet irradiation in an atmosphere containing oxygen may be carried out after forming the metal film as other methods, and furthermore, a thin oxide film may be formed by heating at a temperature of from 200° C. to 350° C. with a clean oven.

An etching rate can be controlled by selecting the metal film and the reactant thusly formed.

The chemical state of the reactant thusly formed over the surface of the metal film may change according to heat treatment or the like in a subsequent process. For example, in the case of forming an oxide film containing W, the valence of tungsten oxide ($WO_x$ (x=2 to 3)) changes.

The metal film and the reactant containing the above metal can be used as a peeling layer.

Subsequently, an insulating film 236 which serves as a base film of a thin film transistor is formed over the silicon oxide film 212. A single layer structure of an insulating film containing oxygen or nitrogen such as silicon oxide (SiOx), silicon nitride (SiNx), silicon oxynitride (SiOxNy) (x>y), or silicon nitride oxide (SiNxOy) (x>y) (x, y=1, 2 . . . ), or a laminated structure thereof can be used for the insulating film 236. For example, in the case of using a laminated structure of two layers, a silicon nitride film 236*a* can be used as a first insulating film, and a silicon oxynitride film 236*b* can be used as a second insulating film. According to these insulating films, impurity diffusion from the first substrate 210 or the like having an insulating surface can be reduced. (Refer to FIG. 7A.)

Subsequently, a semiconductor film is formed and patterned in a predetermined shape to form an island-shaped semiconductor film 214.

The semiconductor film 214 may include any state selected from an amorphous semiconductor, an SAS in which an amorphous state and a crystal state are mixed, a microcrystal semiconductor in which a crystal grain of from 0.5 nm to 20 nm can be observed in an amorphous semiconductor, and a crystalline semiconductor.

In this example, an amorphous semiconductor film is formed to form a crystalline semiconductor film crystallized by heat treatment. Heat treatment can employ a heating furnace, laser irradiation, or light irradiation emitted from a lamp instead of a laser light (hereinafter, referred to as lamp annealing), or a combination thereof can be used.

In the case of using laser irradiation, a continuous oscillation laser beam (CW laser beam) or a pulsed oscillation laser beam (pulsed laser beam) can be used. A laser beam oscillated from one or a plurality of kinds of an Ar laser, a Kr laser, an excimer laser, a YAG laser, a $Y_2O_3$ laser, a $YVO_4$ laser, a YLF laser, a $YAlO_3$ laser, a glass laser, a ruby laser, an alexandrite laser, a Ti: sapphire laser, a copper vapor laser, and a gold vapor laser, can be used as the laser beam. A crystal with a large grain size can be obtained by emitting a laser beam having a fundamental wave of such lasers and/or a second to a fourth harmonic of the fundamental wave. For example, the second harmonic (532 mm) or the third harmonic (355 nm) of an $Nd:YVO_4$ laser (fundamental wave with 1064 nm) can be used. In this case, the power density of laser is required to be approximately from 0.01 $MW/cm^2$ to 100 $MW/cm^2$ (preferably from 0.1 $MW/cm^2$ to 10 $MW/cm^2$) at the scanning rate of approximately from 10 cm/sec to 2000 cm/sec.

In addition, an incident angle θ of the laser beam may be set to be 0°<θ<90° to the semiconductor film. As a result, interference of the laser beam can be prevented.

A laser beam having a fundamental wave of a continuous oscillation laser and a laser beam having a harmonic of a continuous oscillation laser may be emitted. Alternatively, a laser beam having a fundamental wave of a continuous oscillation laser and a laser beam having a harmonic of a pulsed laser may be emitted. Energy can be compensated by emitting a plurality of laser beams.

A pulsed laser beam can be used, which oscillates a laser with a repetition rate that can emit the next pulsed laser light, until the semiconductor film which is melted due to a laser light is solidified. Crystal grains grown continuously in the scanning direction can be obtained by oscillating a laser beam with the frequency. A specific repetition rate of a laser beam is 10 MHz or more, and this is a remarkably higher frequency band than a frequency band of from several tens of Hz to several hundreds of Hz, which is employed generally.

Note that a laser beam may be emitted in an inert gas atmosphere such as a rare gas or nitrogen. Thus, roughness on the semiconductor surface due to the laser beam irradiation can be suppressed, the planarity can be enhanced, and fluctuation on a threshold value generated due to variation of interface state density can be suppressed.

A microcrystalline semiconductor film is formed using $SiH_4$ and $F_2$ or $SiH_4$ and $H_2$, and then the microcrystalline semiconductor film may be crystallized by the laser irradiation described above.

In the case of using a heating furnace as another heat treatment, an amorphous semiconductor film is heated for from 2 hours to 20 hours at from 500° C. to 550° C. At this time, the temperature may be set at multiple stages in the range of from 500° C. to 550° C. in order to raise the temperature higher gradually. Hydrogen or the like comes out from the amorphous semiconductor film by the initial low-temperature heat treatment, and therefore, so-called dehydrogenation which reduces film-roughness generated in the crystallization can be conducted. Further, it is preferable that a metal element for promoting crystallization such as Ni is formed over an amorphous semiconductor film since the heat temperature can be reduced. Even during crystallization when using such a metal element is conducted, the amorphous semiconductor film may be heated at from 600° C. to 950° C.

However, when such a metal element is formed, there is concern that the metal element adversely affects electric characteristics of a semiconductor element, and thus a gettering process for reducing or removing the metal element is required. For example, the metal element may be trapped using an amorphous semiconductor film including Ar, P, and the like as a gettering sink.

In addition, a crystalline semiconductor film may be formed directly on a surface to be formed. In this case, a crystalline semiconductor film can be formed directly on a surface to be formed using a gas containing fluorine such as $GeF_4$ or $F_2$ and a gas containing silane such as $SiH_4$ or $Si_2H_6$ with heat or plasma. When a crystalline semiconductor film is directly formed and high temperature treatment is required, a quartz substrate having high heat resistance may be used.

A semiconductor film thusly formed can be used for a first n-type TFT 215, a second n-type TFT 216, a p-type TFT 217, or a capacitor element 218. A TFT may have any structure, and a single drain structure having a channel region and a high concentration impurity region in the semiconductor film, a LDD structure having a channel region, a high concentration impurity region and a low concentration impurity region in the semiconductor film, or a GOLD structure having a channel region, a high concentration impurity region and a low concentration impurity region in the semiconductor film in which a gate electrode overlaps the low concentration impurity region can be used. This example explains a case where the second n-type TFT 216 and the p-type TFT 1217 has a single drain structure and the first n-type TFT 215 has a LDD structure.

An actual integrated circuit is formed using an n-type TFT or a p-type TFT alone or combining an n-type TFT and a p-type TFT, or using a CMOS TFT in which an n-type TFT and a p-type TFT are combined alone or using a CMOS TFT together with an n-type TFT or a p-type TFT.

First, as shown in FIG. 7A, an impurity element is added to a semiconductor film which is to be the capacitor element 218. In this example, an impurity element having an n-type such as phosphorus (P) can be added. At this time, a semiconductor film of a TFT region is covered with a resist mask 219 so that an impurity element is not added to the semiconductor film.

Then, as shown in FIG. 7B, a gate insulating film 303 is formed. A single layer structure of an insulating film containing oxygen or nitrogen such as silicon oxide (SiOx), silicon nitride (SiNx), silicon oxynitride (SiOxNy) (x>y), or silicon nitride oxide (SiNxOy) (x>y) (x, y=1, 2 . . . ), or a laminated structure thereof can be used for the insulating film. In this example, a silicon nitride film is used. A silicon nitride film has high relative dielectric constant compared with a silicon oxide film. Therefore, the gate insulating film can be more thickened. Gate leak current can be reduced when the gate insulating film is thickened. Since a problem of gate leak current is caused when a TFT or the like is miniaturized, the gate insulating film may be formed using an insulating material having high relative dielectric constant as a TFT or the like is miniaturized.

Then, a conductive film which serves as a gate electrode is formed. A gate electrode 304 may be a single layer or a lamination, and can be formed from an element selected from Ta, W, Ti, Mo, Al, and Cu, or an alloy material or a compound material containing the element as its main component. In this example, a tantalum nitride film is formed to have a film thickness of from 10 nm to 50 nm, for example, 30 nm as a first conductive film 304a, and a tungsten film is sequentially formed to have a film thickness of from 200 nm to 400 nm, for example, 370 nm as a second conductive film 304b.

Then, the first and second conductive films 304a and 304b are etched to have predetermined shapes. In this example, the first and second conductive films 304a and 304b are formed to have tapered shapes in their edge portions. At this time, each angle formed by the first conductive films 304a and the substrate, and the second conductive films 304b and the substrate may be 60°±15°, respectively.

The first and second conductive films 304a and 304b may be further etched, and in this example, the first and second conductive films 304a and 304b are etched so that the tapered shape in the edge portion disappears, in other words, the edge portion is made to be perpendicular to the substrate, as shown in FIG. 7C. At this time, each angle formed by the first conductive films 304a and the substrate, and the second conductive films 304b and the substrate may be 90°±5°, respectively. The first conductive film 304a can be aggressively etched by using an etching agent which has different etching rate of the first conductive film 304a from that of the second conductive film 304b.

The width of the conductive film may be shortened to form a TFT having a miniaturized gate length. Therefore, a step for thinning a mask provided to etch the conductive film, for example, a resist mask may be carried out. For example, the resist mask can be thinned by oxygen plasma.

As shown in FIG. 8A, a mask covering the p-type TFT 217, for example, a resist mask 220 is formed. Then, an element imparting an n-type such as phosphorus (P) is added to the semiconductor film 214. Thus, a low concentration impurity region 221 is formed by controlling the amount of element addition. And then, the resist mask 220 is removed.

Subsequently, as shown in FIG. 8B, a mask covering a part of the first n-type TFT 215, for example, a resist mask 222 is formed. Then, an element imparting an n-type is added to the semiconductor film 214. Thus, a high concentration impurity region 223 is formed by controlling the amount of element addition. At this time, a whole impurity region included in the second n-type TFT 216 can be a high concentration impurity region since the first conductive film 304a is extremely thin. A high concentration impurity region may be formed by adding the element after forming a resist covering only the second conductive film 304b of the second n-type TFT 216 at the same time as forming the resist mask 222.

In addition, a high concentration impurity region may be formed by providing a sidewall instead of the resist mask 222.

At this time, the resist mask 220 is formed again so that the element is not added to a p-type TFT. Alternatively, the resist mask 220 may be used without being removed in a previous step.

Then, as shown in FIG. 8C, a mask covering the n-type TFTs 215 and 216 and the capacitor element 218, for example, a resist mask 224 is formed to form the p-type TFT 217. Then, an element imparting a p-type such as boron (B) is added to the semiconductor film 214. At this time, an impurity region 229 can be formed by controlling the amount of element addition. Here, the impurity region is not expressed by using a term of "high concentration" or "low concentration" since high or low of the impurity concentration is relative and the impurity region of the p-type TFT has one kind of concentration.

Subsequently, heat treatment is arbitrarily carried out to modify a defect of the semiconductor film. For example, as shown in FIG. 9A, heat treatment can be carried out after an insulating film 225 and an insulating film 226 are sequentially formed. An insulating film containing oxygen or nitrogen such as silicon oxide (SiOx), silicon nitride (SiNx), silicon oxynitride (SiOxNy) (x>y), or silicon nitride oxide (SiNxoy) (x>y) (x, y=1, 2 . . . ) can be used for the insulating films 225 and 226. In this example, SiON is used for the insulating film 225 and SiNO is used for the insulating film 226. According to hydrogen included in these insulating films, a dangling bond of the semiconductor film can be reduced.

Planarity can be enhanced by forming an interlayer insulating film 227. An organic material, an inorganic material, siloxane, or polysilazane can be used for the interlayer insulating film. Polyimide, acrylic, polyamide, polyimide amide, a resist, or benzocyclobutene can be used as the organic material. Siloxane has a skeleton structure with a bond of silicon (Si) and oxygen (O). An organic group including at least hydrogen (for example, an alkyl group or aromatic hydrocarbon) is used as a substituent thereof. Further, a fluoro group may be used for the substituent. Also, an organic group including at least hydrogen and a fluoro group may be used for the substituent. Siloxane is formed by using a polymer material having at least one kind of the substituents described above as a starting material. Polysilazane is formed by using a liquid material including a polymer material having a bond of silicon (Si) and nitrogen (N), which is a so-called polysilazane, as a starting material. An insulating film containing oxygen or nitrogen such as silicon oxide (SiOx), silicon nitride (SiNx), silicon oxynitride (SiOxNy) (x>y), or silicon nitride oxide (SiNxOy) (x>y) (x, y=1, 2 . . . ) can be used as the inorganic material. In addition, a laminated structure of the insulating films described above may be used for the interlayer insulating film. In particular, when the interlayer insulating film is formed using an organic material, planarity is enhanced; however, water and oxygen are absorbed by an organic material. Therefore, an insulating film containing an inorganic material is preferably formed over the organic material to prevent the absorption of water and oxygen. When an insulating film containing nitrogen is used for the inorganic material, the intrusion of an alkali ion such as Na can be prevented.

An opening is formed in the interlayer insulating film 227, the insulating films 225 and 226, and the gate insulating film 303 so as to expose the high concentration impurity region 223 and the impurity region 229. Then, a conductive film 228 which serves as a wiring is formed in the opening.

Then, an insulating film which serves as a protective film may be formed. The insulating film which serves as the protective film preferably includes nitrogen.

In the state where a thin film transistor is thusly formed, an opening 232 which exposes the surface of the peeling layer (here, the metal oxide film 213) is formed in a region other than the element formation regions (215 to 218) provided with a TFT, a capacitor element, or the like. In this example, the opening 232 is formed between the p-type TFT 217 and the capacitor element 218. Then, in the similar way as in FIG. 6B, a support substrate 233 provided with a hole 234 is fixed over the first substrate 210 with an adhesive agent or the like (FIG. 9B). A resin material such as an ultraviolet curable resin or a thermosetting resin, or a two-sided tape, or the like can be used as the adhesive agent.

Then, an etchant is introduced into the opening 232 through the hole 234 to remove the peeling layer. The peeling layer in this example includes the metal film 211 formed over the insulating substrate and the metal oxide film 213 which is a reactant thereof, and the insulating substrate can be peeled by removing the metal film and the metal oxide film (FIG. 9B). In the case of using a metal film for the peeling layer, the support substrate 233 can be peeled when at least the metal oxide film 213 reacts with the etchant and is removed.

Gas or liquid containing halogen fluoride can be used as an etchant to be able to chemically remove the peeling layer. For example, $ClF_3$ (chlorine trifluoride) can be used as halogen fluoride. Especially, it is preferable that the peeling layer is W and $WO_3$ which is oxide thereof since $WO_3$ has high reaction speed with $ClF_3$ and the peeling layer can be removed in a short time. Removing the peeling layer chemically with an etching agent is preferable since the generation of a reacted residue or the like can be reduced.

There is a method for removing the peeling layer physically by adding stress, in addition to the method for removing the peeling layer chemically as described above. Especially, in the case where the oxide film containing W is formed as described above, tungsten oxide ($WO_x$ (x=2 to 3)) is preferable since tungsten oxide becomes a condition of being easily peeled by a physical means when the valence changes.

Further, the method for removing chemically and the method for removing physically may be combined. As a result, the peeling layer can be peeled more easily in a short time.

Thus, the peeling layer is removed, the first substrate 210 is peeled. Then, the element formation regions (215 to 218) can be fixed over a flexible substrate such as a plastic substrate or a plastic film substrate which is separately prepared, with an adhesive agent. A resin material such as an ultraviolet curable resin or a thermosetting resin, or a two-sided tape, or the like can be used as the adhesive agent.

In the case of forming a wireless memory or a biological signal processing unit, the first substrate 210 can be reused. Consequently, a manufacturing cost of a wireless memory or the like can be reduced. Further, the substrate provided with the element formation region is not required to transmit laser light; therefore, the degree of freedom of design can be improved.

EXAMPLE 6

In this example, another structure of a TFT used for a wireless memory or a biological signal processing unit and a manufacturing method thereof is described.

Figure 10A:
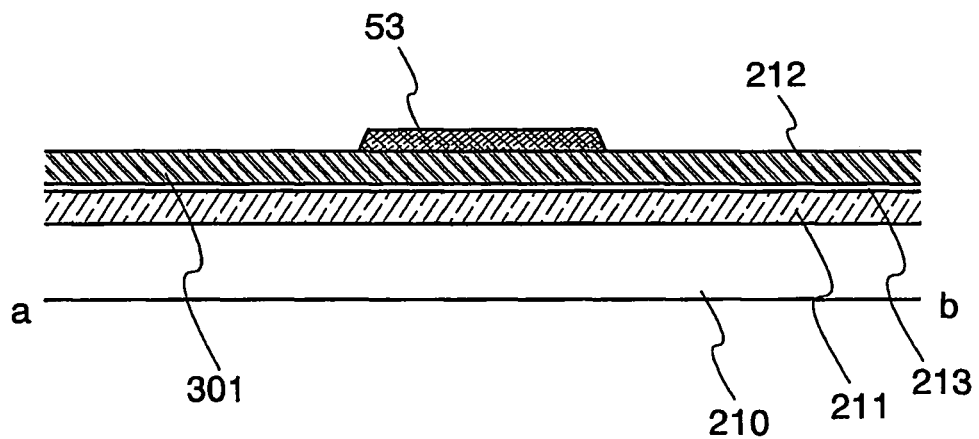
FIGS. 10A and 10B are views of a manufacturing step of a dual gate type TFT used for a wireless memory or the like related to the invention.

As shown in FIG. 10A, a metal film 211 and a silicon oxide film 212 are sequentially provided over a first substrate 210 having an insulating surface, to form a metal oxide film 213 containing the metal. For example, in the case of using W for the metal film, the metal oxide film 213 ($WO_x$ (x=2 to 3)) containing W is formed. Then, a lower electrode 53 of a TFT is formed. The lower electrode 53 can be formed by a polycrystalline semiconductor in which metal or an impurity of one conductive type is added. In the case of using metal, tungsten (W), molybdenum (Mo), titanium (Ti), tantalum (Ta), aluminum (Al), or the like can be used. The lower electrode 53 is etched in a predetermined shape using a mask (for example, a resist mask). At this time, for example, the resist mask can be thinned by oxygen plasma. According to the step as described above, the lower electrode 53 which is to be a gate electrode can be thinned (tapered).

Figure 10B:
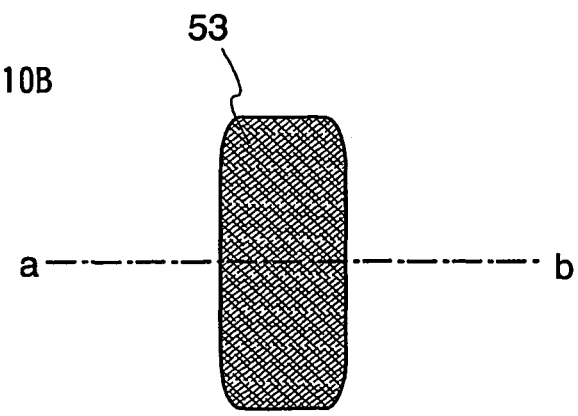

FIG. 10B shows a top view of the lower electrode 53, and a cross section of FIG. 10B taken along line a-b corresponds to FIG. 10A.

Figure 11A:
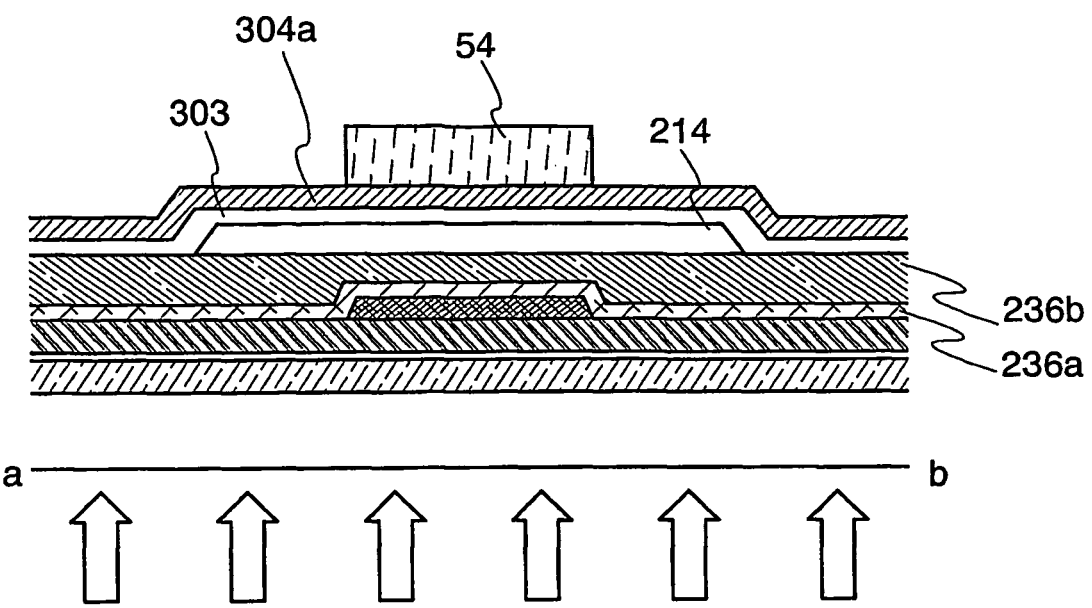
FIGS. 11A and 11B are views of a manufacturing step of a dual gate type TFT used for a wireless memory or the like related to the invention.

Then, as shown in FIG. 11A, an insulating film 236 which serves as a base film is formed. In this example, a silicon nitride film 236a is formed as a first insulating film and a silicon oxynitride film 236b is formed as a second insulating film; however, the insulating film is not limited to this lamination sequence.

Then, a semiconductor film 214 having a predetermined shape, a gate insulating film 303 provided so as to cover the semiconductor film, and a conductive film 304a which serves as a gate electrode are sequentially provided. A mask, for example, a resist mask is formed to pattern the conductive film 304a in a predetermined shape. At this time, a resist mask 54 having a predetermined shape can be formed by rear-surface exposing using the lower electrode 53. Then, the conductive film 304a is patterned in a predetermined shape using the resist mask 54.

Figure 11B:
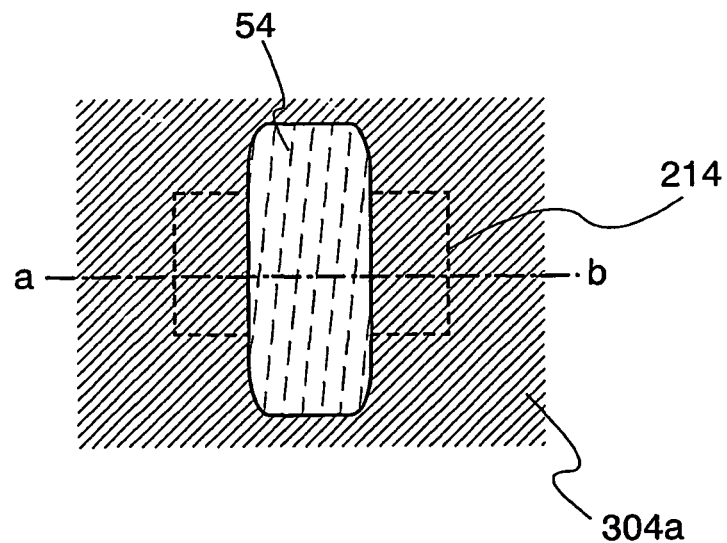

FIG. 11B shows a top view in which the resist mask is provided over a conductive film 304a, and a cross section of FIG. 11B taken along line a-b corresponds to FIG. 11A.

Figure 12A:
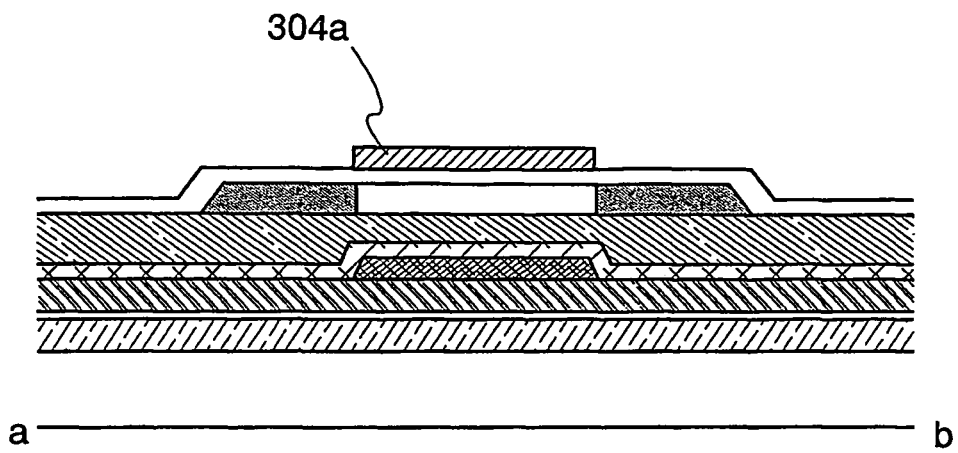
FIGS. 12A and 12B are views of a manufacturing step of a dual gate type TFT used for a wireless memory or the like related to the invention.

Then, as shown in FIG. 12A, an impurity element is added to the semiconductor film 214 using the patterned conductive film 304a as a mask.

Each of the lower electrode 53 and the conductive film 304a is provided with a wiring to be separately controlled. At this time, a part of the conductive film 304a is removed to provide a contact hole which connects the lower electrode 53 to the wiring. The part of the conductive film 304a may be etched by providing a mask, for example, a resist mask over the conductive film 304a.

Figure 12B:
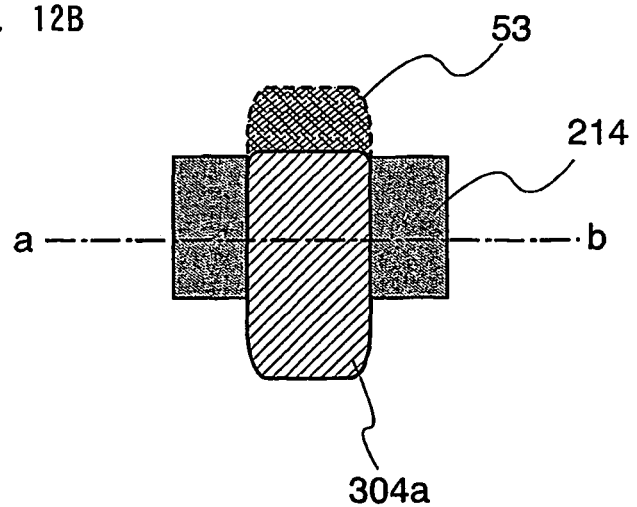

FIG. 12B shows a top view of the conductive film 304a in which a part thereof is etched, and a cross section of FIG. 12B taken along line a-b corresponds to FIG. 12A.

In the case of controlling the lower electrode 53 and the conductive film 304a in the similar way, a part of the conductive film 304a is not required to be removed as described above. The lower electrode 53 and the conductive film 304a can be connected to each other by forming a contact hole in the gate insulating film 303 provided over the lower electrode 53 and then forming the conductive film 304a in the contact hole.

Figure 13A:
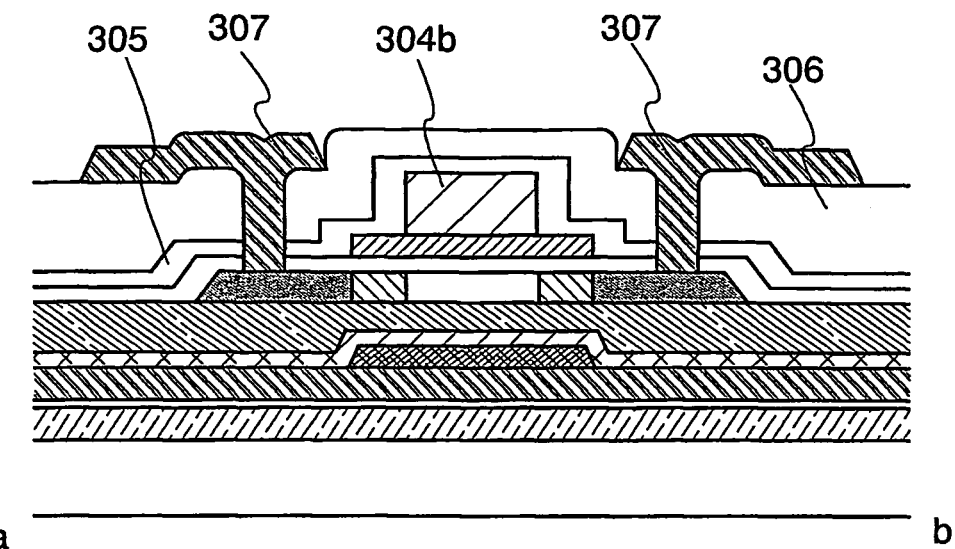
FIGS. 13A and 13B are views of a manufacturing step of a dual gate type TFT used for a wireless memory or the like related to the invention.

Then, as shown in FIG. 13A, a conductive film 304b may be formed to make the gate electrode to be a laminated structure. In this example, the conductive film 304b can be patterned in a predetermined shape using a mask, for example, a resist mask. An impurity element may be added in the state where the conductive film 304b is provided. At this time, a low concentration impurity region can be formed so that the conductive film 304a overlaps the low concentration impurity region.

Then, an insulating film 305 is formed to cover the gate electrode. An insulating film containing oxygen or nitrogen such as silicon oxide (SiOx), silicon nitride (SiNx), silicon oxynitride (SiOxNy) (x>y), or silicon nitride oxide (SiNxOy) (x>y) (x, y=1, 2 . . . ) can be used for the insulating film 305. In this example, silicon oxynitride is used. Especially, by forming the insulating film 305 by a plasma CVD method, the large amount of hydrogen can be included therein. It is preferable since a dangling bond of the semiconductor film 214 can be reduced due to the hydrogen. Therefore, heat treatment may be carried out in the state where the insulating film 305 is provided.

Planarity can be enhanced by forming an interlayer insulating film 306 which covers the insulating film 305. An organic material, an inorganic material, or siloxane, or polysilazane can be used for the interlayer insulating film 305. Polyimide, acrylic, polyamide, polyimide amide, a resist, or benzocyclobutene can be used as the organic material as described above. A laminated structure of the insulating films described above may be used for the interlayer insulating film. Especially, when the interlayer insulating film is formed using an organic material, planarity is improved; however, water and oxygen are absorbed by an organic material. Therefore, an insulating film containing an inorganic material is preferably formed over the organic material to prevent the absorption of water and oxygen. When an insulating film containing nitrogen is used for the inorganic material, the intrusion of an alkali ion such as Na can be prevented.

Heat treatment after forming the insulating film 305 may be carried out after forming the interlayer insulating film 306.

Then, a contact hole is formed in the interlayer insulating film 306, the insulating film 305, and the gate insulating film 303 to form a wiring 307 which is to be connected to the impurity region.

Further, an insulating film which serves as a protective film may be formed over the wiring. An insulating film containing oxygen or nitrogen such as silicon oxide (SiOx), silicon nitride (SiNx), silicon oxynitride (SiOxNy) (x>y), or silicon nitride oxide (SiNxOy) (x>y) (x, y=1, 2 . . . ) can be used for the insulating film. Especially, an insulating film containing nitrogen is preferably used to prevent intrusion of an impurity element.

Figure 13B:
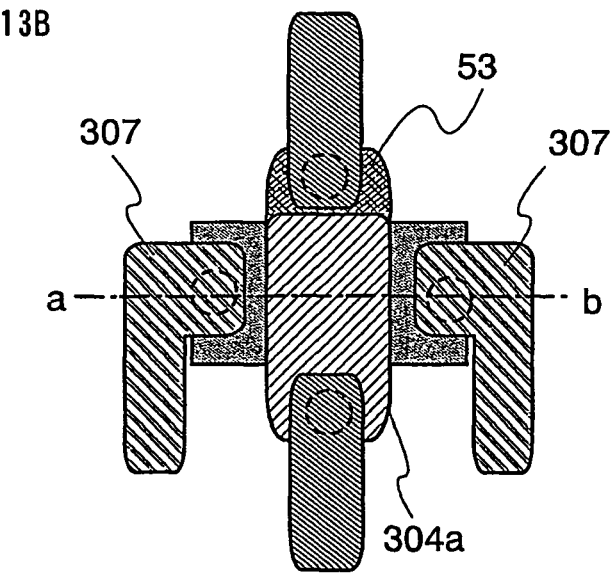

FIG. 13B shows a top view in which the wiring 307, a wiring connected to the lower electrode, and a wiring connected to the gate electrode are provided, and a cross section of FIG. 13B taken along line a-b corresponds to FIG. 13A. The conductive film 304b is not shown.

Thus, a so-called dual gate type TFT having the lower electrode 53 and upper electrode (including the conductive films 304a and 304b) can be formed. In the case of a TFT having the lower electrode, the lower electrode can be controlled separately from the gate electrode. Therefore, in the case of forming a miniaturized TFT; current is subject to flow even when a signal which is made to be OFF is inputted to the gate electrode. At this time, the TFT can be precisely an OFF state by controlling the lower electrode. As a result, power consumption can be reduced. Further, threshold voltage (Vth) can be controlled by the lower electrode.

INDUSTRIAL APPLICABILITY

In the above-mentioned embodiments and examples, a case where a brain wave is detected as a biological signal is described; however, any other biological signals can be detected, processed, and controlled according to the invention. For example, the following biological signals which are to be a measuring object can be given: electrocardiogram, pneumogram, blood pressure, tissue blood volume/blood flow volume, cerebral blood volume, cerebral blood flow velocity, eye movement, electrogastrogram, pupillary reflex, cardiac output, GSR (Galvanic Skin Response), finger tip plethysmogram, percutaneous oxygen/carbon dioxide partial pressure, arterial oxygen saturation, intracerebral pressure variation, or muscle sympathetic nerve activity/electromyogram, or the like. Thus, the present invention has extremely wide ranging application fields.

This application is based on Japanese Patent Application serial No. 2004-210405 field in Japan Patent Office on Jul. 16, 2004, the contents of which are hereby incorporated by reference.

The invention claimed is:
1. A biological signal processing unit comprising:
an electrode for at least one of detecting a biological signal from an inside of a living body and transmitting an electric signal to the inside of the living body;
a plastic substrate having flexibility;
an antenna over the plastic substrate having flexibility, wherein the antenna is configured to wirelessly communicate with a wireless memory configured to be attached to the living body, which is located outside the biological signal processing unit;
an interface comprising a rectification circuit provided between the electrode and the antenna and over the plastic substrate having flexibility; and
a processor over the plastic substrate having flexibility, wherein the processor comprises a transistor electrically connected to the antenna, the transistor comprising:
a first insulating film;
a first electrode over the first insulating film;
a second insulating film over the first insulating film and the first electrode;
a semiconductor layer over the second insulating film, so as to overlap with the first electrode, wherein the semiconductor layer comprises a channel region, a first impurity region, and a second impurity region between the channel region and the first impurity region, and wherein a concentration of an impurity element in the second impurity region is lower than a concentration of the impurity element in the first impurity region;
a third insulating film over the semiconductor layer;
a second electrode over the third insulating film, so as to overlap with the semiconductor layer;

a third electrode over the second electrode, wherein a width of the third electrode is shorter than a width of the second electrode in a channel length direction;
a fourth insulating film over the third insulating film, second electrode and the third electrode; and
a fourth electrode over the fourth insulating film, the fourth electrode electrically connected to the first impurity region through a contact hole in the third insulating film and the fourth insulating film,
wherein at least the antenna, the rectification circuit, and the processor are provided over the plastic substrate having flexibility with an adhesive agent interposed therebetween.

2. The biological signal processing unit according to claim 1, wherein the plastic substrate comprises one selected from the group consisting of polyethylene terephthalate, polycarbonate, polyarylate, and polyethersulfone.

3. The biological signal processing unit according to claim 1, wherein the second impurity region is overlapped with the second electrode and is not overlapped with the third electrode.

4. A biological signal processing unit comprising:
an electrode for transmitting an electric signal including information to an inside of a living body;
a plastic substrate having flexibility;
an antenna over the plastic substrate having flexibility, the antenna configured to wirelessly communicate with a reader/writer located outside of the living body;
an interface comprising a rectification circuit provided between the electrode and the antenna and over the plastic substrate having flexibility; and
a processor over the plastic substrate having flexibility, wherein the processor comprises a transistor, the transistor comprising:
a first insulating film;
a first electrode over the first insulating film;
a second insulating film over the first insulating film and the first electrode;
a semiconductor layer over the second insulating film, so as to overlap with the first electrode, wherein the semiconductor layer comprises a channel region, a first impurity region, and a second impurity region between the channel region and the first impurity region, and wherein a concentration of an impurity element in the second impurity region is lower than a concentration of the impurity element in the first impurity region;
a third insulating film over the semiconductor layer;
a second electrode over the third insulating film, so as to overlap with the semiconductor layer;
a third electrode over the second electrode, wherein a width of the third electrode is shorter than a width of the second electrode in a channel length direction;
a fourth insulating film over the third insulating film, second electrode and the third electrode; and
a fourth electrode over the fourth insulating film, the fourth electrode electrically connected to the first impurity region through a contact hole in the third insulating film and the fourth insulating film,
wherein at least the antenna, the rectification circuit, and the processor are provided over the plastic substrate having flexibility with an adhesive agent interposed therebetween.

5. The biological signal processing unit according to claim 4, wherein the electric signal including information is a brain wave.

6. The biological signal processing unit according to claim 4, wherein the plastic substrate comprises one selected from the group consisting of polyethylene terephthalate, polycarbonate, polyarylate, and polyethersulfone.

7. The biological signal processing unit according to claim 4, wherein the second impurity region is overlapped with the second electrode and is not overlapped with the third electrode.

8. A helmet including the biological signal processing unit according to any one of claim 1 and claim 4.

9. A hat including the biological signal processing unit according to any any one of claim 1 and claim 4.

10. A pair of glasses including the biological signal processing unit according to any one of claim 1 and claim 4.

11. A headphone including the biological signal processing unit according to any one of claim 1 and claim 4.

12. An accessory including the biological signal processing unit according to any one of claim 1 and claim 4.

13. A wireless memory comprising:
a plastic substrate having flexibility;
a memory element over the plastic substrate having flexibility, wherein the memory element is configured to memorize information on an electric signal transmitted to an inside of a living body, and wherein the memory element comprises a transistor, the transistor comprising:
a first insulating film;
a first electrode over the first insulating film;
a second insulating film over the first insulating film and the first electrode;
a semiconductor layer over the second insulating film, so as to overlap with the first electrode, wherein the semiconductor layer comprises a channel region, a first impurity region, and a second impurity region between the channel region and the first impurity region, and wherein a concentration of an impurity element in the second impurity region is lower than a concentration of the impurity element in the first impurity region;
a third insulating film over the semiconductor layer;
a second electrode over the third insulating film, so as to overlap with the semiconductor layer;
a third electrode over the second electrode, wherein a width of the third electrode is shorter than a width of the second electrode in a channel length direction;
a fourth insulating film over the third insulating film, second electrode and the third electrode; and
a fourth electrode over the fourth insulating film, the fourth electrode electrically connected to the first impurity region through a contact hole in the third insulating film and the fourth insulating film; and
an antenna configured to communicate with a biological signal processing unit located outside the wireless memory,
wherein the wireless memory is configured to be attached to the living body, and
wherein the memory element and the antenna are provided over the plastic substrate having flexibility with an adhesive agent interposed therebetween.

14. The wireless memory according to claim 13, wherein the second impurity region is overlapped with the second electrode and is not overlapped with the third electrode.

15. A biological signal processing system comprising:
a biological signal processing unit comprising,
an electrode and a first interface for transmitting an electric signal including first information to an inside of a living body, a first antenna configured to wirelessly communicate with a wireless memory configured to be attached to the living body; and
a second interface comprising a rectification circuit; and
the wireless memory comprising,
a plastic substrate having flexibility;
a memory element over the plastic substrate having flexibility, wherein the memory element is configured to memorize second information on the electric signal transmitted to the inside of the living body, and wherein the memory element comprises a transistor, the transistor comprising:
a first insulating film;
a first electrode over the first insulating film;
a second insulating film over the first insulating film and the first electrode;
a semiconductor layer over the second insulating film, so as to overlap with the first electrode, wherein the semiconductor layer comprises a channel region, a first impurity region, and a second impurity region between the channel region and the first impurity region, and wherein a concentration of an impurity element in the second impurity region is lower than a concentration of the impurity element in the first impurity region;
a third insulating film over the semiconductor layer;
a second electrode over the third insulating film, so as to overlap with the semiconductor layer;
a third electrode over the second electrode, wherein a width of the third electrode is shorter than a width of the second electrode in a channel length direction;
a fourth insulating film over the third insulating film, second electrode and the third electrode; and
a fourth electrode over the fourth insulating film, the fourth electrode electrically connected to the first impurity region through a contact hole in the third insulating film and the fourth insulating film; and
a second antenna over the plastic substrate having flexibility configured to wirelessly communicate with the biological signal processing unit,
wherein the memory element and the second antenna are provided over the plastic substrate having flexibility with an adhesive agent interposed therebetween.

16. The biological signal processing unit according to claim 15, wherein the electric signal including first information is a brain wave.

17. The biological signal processing system according to claim 15, wherein the plastic substrate comprises one selected from the group consisting of polyethylene terephthalate, polycarbonate, polyarylate, and polyethersulfone.

18. The biological signal processing system according to claim 15, wherein the second impurity region is overlapped with the second electrode and is not overlapped with the third electrode.

19. A control system of a device to be controlled comprising:
a biological signal processing unit comprising:
an electrode and a first interface for detecting an electric signal from an inside of a living body:
a plastic substrate having flexibility;
an antenna over the plastic substrate having flexibility, wherein the antenna is configured to wirelessly communicate with a reader/writer located outside of the living body;
a second interface comprising a rectification circuit over the plastic substrate having flexibility; and
a processor over the plastic substrate having flexibility, wherein the processor comprises a transistor electrically connected to the antenna, the transistor comprising:
a first insulating film;
a first electrode over the first insulating film;
a second insulating film over the first insulating film and the first electrode;
a semiconductor layer over the second insulating film, so as to overlap with the first electrode, wherein the semiconductor layer comprises a channel region, a first impurity region, and a second impurity region between the channel region and the first impurity region, and wherein a concentration of an impurity element in the second impurity region is lower than a concentration of the impurity element in the first impurity region;
a third insulating film over the semiconductor layer;
a second electrode over the third insulating film, so as to overlap with the semiconductor layer;
a third electrode over the second electrode, wherein a width of the third electrode is shorter than a width of the second electrode in a channel length direction;
a fourth insulating film over the third insulating film, second electrode and the third electrode; and
a fourth electrode over the fourth insulating film, the fourth electrode electrically connected to the first impurity region through a contact hole in the third insulating film and the fourth insulating film,
wherein the antenna and the processor are provided over the plastic substrate having flexibility with an adhesive agent interposed therebetween;
the reader/writer configured to wirelessly communicate with the biological signal processing unit; and
a device to be controlled connected to the reader/writer,
wherein the device to be controlled can be controlled based on the electric signal, which is transmitted from the inside of the living body to the device to be controlled through the reader/writer.

20. The control system according to claim 19, wherein the device to be controlled is one selected from the group consisting of an electronic device and a mobile object.

21. The control system according to claim 19, wherein the plastic substrate comprises one selected from the group consisting of polyethylene terephthalate, polycarbonate, polyarylate, and polyethersulfone.

22. The control system according to claim 19, wherein the second impurity region is overlapped with the second electrode and is not overlapped with the third electrode.

23. A biological signal processing unit comprising:
an electrode for at least one of detecting a biological signal from an inside of a living body and transmitting an electric signal to the inside of the living body;
a plastic substrate having flexibility;
an antenna over the plastic substrate having flexibility, wherein the antenna is configured to wirelessly communicate with a wireless memory configured to be attached to the living body, which is located outside the biological signal processing unit;
an interface comprising a rectification circuit over the plastic substrate having flexibility; and
a means for processing at least one of the biological signal and the electric signal provided between the electrode and the antenna and provided over the plastic substrate having flexibility, wherein the means comprises a transistor electrically connected to the antenna, the transistor comprising:
a first insulating film;
a first electrode over the first insulating film;
a second insulating film over the first insulating film and the first electrode;
a semiconductor layer over the second insulating film, so as to overlap with the first electrode, wherein the semiconductor layer comprises a channel region, a first impurity region, and a second impurity region between the channel region and the first impurity region, and wherein a concentration of an impurity element in the second impurity region is lower than a concentration of the impurity element in the first impurity region;
a third insulating film over the semiconductor layer;
a second electrode over the third insulating film, so as to overlap with the semiconductor layer;
a third electrode over the second electrode, wherein a width of the third electrode is shorter than a width of the second electrode in a channel length direction;
a fourth insulating film over the third insulating film, second electrode and the third electrode; and
a fourth electrode over the fourth insulating film, the fourth electrode electrically connected to the first impurity region through a contact hole in the third insulating film and the fourth insulating film, and
wherein the antenna and the means for processing at least one of the biological signal and the electric signal are provided over the plastic substrate having flexibility with an adhesive agent interposed therebetween.

24. The biological signal processing unit according to claim 23, wherein the plastic substrate comprises one selected from the group consisting of polyethylene terephthalate, polycarbonate, polyarylate, and polyethersulfone.

25. The biological signal processing unit according to claim 23, wherein the second impurity region is overlapped with the second electrode and is not overlapped with the third electrode.

26. A biological signal processing unit comprising:
an electrode for transmitting an electric signal including information to an inside of a living body;
a plastic substrate having flexibility;
an antenna over the plastic substrate having flexibility, the antenna configured to wirelessly communicate with a reader/writer located outside of the living body;
an interface comprising a rectification circuit over the plastic substrate having flexibility; and
a means for processing at least one of a biological signal detected from the inside of the living body and the electric signal provided between the electrode and the antenna and provided over the plastic substrate having flexibility,
wherein the means comprises a transistor electrically connected to the antenna, the transistor comprising:
a first insulating film;
a first electrode over the first insulating film;
a second insulating film over the first insulating film and the first electrode;
a semiconductor layer over the second insulating film, so as to overlap with the first electrode, wherein the semiconductor layer comprises a channel region, a first impurity region, and a second impurity region between the channel region and the first impurity region, and wherein a concentration of an impurity element in the second impurity region is lower than a concentration of the impurity element in the first impurity region;
a third insulating film over the semiconductor layer;
a second electrode over the third insulating film, so as to overlap with the semiconductor layer;
a third electrode over the second electrode, wherein a width of the third electrode is shorter than a width of the second electrode in a channel length direction;
a fourth insulating film over the third insulating film, second electrode and the third electrode; and
a fourth electrode over the fourth insulating film, the fourth electrode electrically connected to the first impurity region through a contact hole in the third insulating film and the fourth insulating film, and
wherein the antenna and the means for processing at least one of the biological signal and the electric signal are provided over the plastic substrate having flexibility with an adhesive agent interposed therebetween.

27. The biological signal processing unit according to claim 26, wherein the electric signal including information is a brain wave.

28. The biological signal processing unit according to claim 26, wherein the plastic substrate comprises one selected from the group consisting of polyethylene terephthalate, polycarbonate, polyarylate, and polyethersulfone.

29. The biological signal processing unit according to claim 26, wherein the second impurity region is overlapped with the second electrode and is not overlapped with the third electrode.

30. A helmet including the biological signal processing unit according to any one of claim 23 and claim 26.

31. A hat including the biological signal processing unit according to any one of claim 23 and claim 26.

32. A pair of glasses including the biological signal processing unit according to any one of claim 23 and claim 26.

33. A headphone including the biological signal processing unit according to any one of claim 23 and claim 26.

34. An accessory including the biological signal processing unit according to any one of claim 23 and claim 26.

* * * * *

UNITED STATES PATENT AND TRADEMARK OFFICE
CERTIFICATE OF CORRECTION

PATENT NO. : 8,818,497 B2
APPLICATION NO. : 11/631159
DATED : August 26, 2014
INVENTOR(S) : Shunpei Yamazaki Page 1 of 1

It is certified that error appears in the above-identified patent and that said Letters Patent is hereby corrected as shown below:

In the Specification

At column 5, line 35, "hereinafter," should be --(hereinafter,--;

At column 13, line 18, "semiconductor SAS" should be --semiconductor. SAS--;

At column 14, line 27, "Ni," should be --Ti,--;

At column 15, line 65, "(532 mm)" should be --(532 nm)--;

At column 17, line 9, "1217" should be --217--;

At column 18, line 47, "(SiNxoy)" should be --(SiNxOy)--;

At column 22, line 6, "TFT;" should be --TFT,--;

In the Claims

In claim 9, at column 24, line 12, "any any one" should be --any one--;

In claim 19, at column 25, line 60, "body:" should be --body;--.

Signed and Sealed this
Twenty-first Day of July, 2015

Michelle K. Lee
*Director of the United States Patent and Trademark Office*